United States Patent
Murali et al.

(10) Patent No.: US 9,751,830 B2
(45) Date of Patent: Sep. 5, 2017

(54) INHIBITORS OF THE TUMOR NECROSIS FACTOR RECEPTOR COMPLEX

(75) Inventors: Ramachandran Murali, Beverly Hills, CA (US); Mark I. Greene, Penn Valley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1343 days.

(21) Appl. No.: 13/634,368

(22) PCT Filed: Mar. 7, 2011

(86) PCT No.: PCT/US2011/027371
§ 371 (c)(1),
(2), (4) Date: Nov. 19, 2012

(87) PCT Pub. No.: WO2011/115763
PCT Pub. Date: Sep. 22, 2011

(65) Prior Publication Data
US 2015/0368187 A1    Dec. 24, 2015

Related U.S. Application Data

(60) Provisional application No. 61/313,870, filed on Mar. 15, 2010.

(51) Int. Cl.
| | | |
|---|---|---|
| C07C 233/25 | (2006.01) | |
| A61K 31/075 | (2006.01) | |
| C07C 217/18 | (2006.01) | |
| C07C 217/20 | (2006.01) | |
| C07C 233/18 | (2006.01) | |
| C07C 217/32 | (2006.01) | |

(52) U.S. Cl.
CPC .......... *C07C 233/25* (2013.01); *A61K 31/075* (2013.01); *C07C 217/18* (2013.01); *C07C 217/20* (2013.01); *C07C 217/32* (2013.01); *C07C 233/18* (2013.01)

(58) Field of Classification Search
None
See application file for complete search history.

(56) References Cited

U.S. PATENT DOCUMENTS

| | | |
|---|---|---|
| 3,959,273 A | 5/1976 | Mallion et al. |
| 4,041,075 A | 8/1977 | Smith |
| 4,579,861 A | 4/1986 | Casagrande et al. |
| 4,927,836 A | 5/1990 | Holloway et al. |
| 2005/0043371 A1 | 2/2005 | Taniguchi et al. |
| 2007/0276034 A1 | 11/2007 | Esposito et al. |
| 2009/0221527 A1 | 9/2009 | Greene et al. |

FOREIGN PATENT DOCUMENTS

| | | |
|---|---|---|
| JP | 10-175913 | 6/1998 |
| WO | WO 2006/083970 | 8/2006 |

OTHER PUBLICATIONS

Banner et al., "Crystal Structure of the Soluble Human 55 kd TNF Receptor-Human TNF β Complex: Implications for TNF Receptor Activation", Cell, May 7, 1993, 73(3), 431-445.
Berge et al., "Pharmaceutical Salts," J. Pharm. Sci., Jan. 1977, 66(1), 1-19.
International Patent Application No. PCT/US2011/027371: International Search Report and Written Opinion dated Apr. 22, 2011, 9 pages.
Murali et al., "Disabling TNF receptor signaling by induced conformational perturbation of tryptophan-107," PNAS, Aug. 2005, 102(31), 10970-10975.

*Primary Examiner* — Clinton Brooks
(74) *Attorney, Agent, or Firm* — Baker & Hostetler LLP

(57) ABSTRACT

The present invention relates to compounds of formula (I) that are inhibitors of tumor necrosis factor receptor I, compositions comprising such compounds, and methods of using such compounds and compositions thereof in the treatment of TNF-α mediated conditions: Formula (I)

41 Claims, 5 Drawing Sheets

INHIBITORS OF THE TUMOR NECROSIS FACTOR RECEPTOR COMPLEX

CROSS-REFERENCE TO RELATED APPLICATIONS

This application is the National Stage of International Application No. PCT/US2011/027371, filed Mar. 7, 2011, which claims the benefit of U.S. Provisional Application No. 61/313,870 filed Mar. 15, 2010, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 4, 2017, is named 103241_005787_SL.txt and is 1,887 bytes in size.

TECHNICAL FIELD

The present invention relates to compounds that are inhibitors of tumor necrosis factor receptor I and methods of use thereof.

BACKGROUND

The tumor necrosis factor and receptor family subserve many fundamental biological functions. The tumor necrosis factor receptor (TNF-R) is a central mediator of inflammation. Tumor necrosis factor α (TNF-α) is a pro-inflammatory cytokine as a ligand for TNF-R. Blocking TNF-α and TNF-R is beneficial for the treatment of rheumatoid arthritis, stroke, and other inflammatory diseases.

TNF-α is a pleiotropic cytokine produced by activated macrophages/monocytes and lymphocytes. TNF-α is a potent mediator in inflammatory and immune responses, including the recruitment of leukocytes to injured tissues during bacterial and other microbial infections, and following stimulation with inflammatory substances. When present in excessive quantities, TNF-α is known to cause tissue injury, and has been implicated in the pathology associated with inflammatory and autoimmune diseases.

The biological effects of TNF-α, are mediated through two distinct membrane-protein receptors, TNF-RI and TNF-RII (in humans, p55 and p75, respectively), which differ in sequence and molecular mass. TNF-RI is reported to be present at low levels in most, if not all, human cell types, and expression of the TNF-RI gene in humans can be upregulated by infection, interferons, and modulators of second messengers, such as phorbol esters. The extracellular portions of both TNF receptors also exist in soluble forms, which are derived from membrane-bound forms of the receptors by proteolytic cleavage at the cell surface. The soluble TNF receptors retain the ability to bind TNF-α in solution. Soluble TNF receptors have been identified in urine and sera from healthy individuals, and have been shown to be elevated in some chronic diseases and following inoculation with agents that induce TNF-α release.

The pathological effects of TNF-α can be alleviated by administration of soluble TNF-R fragments or anti-TNF-α antibodies. These agents bind circulating TNF-α, thus preventing the binding of TNF-α to TNF-R and lowering TNF-α signaling. TNF-R fragments or anti-TNF-α antibodies have been approved, by the U.S. Food and Drug Administration, for treatment of rheumatoid arthritis, juvenile rheumatoid arthritis, ankylosing spondylitis, psoriatic arthritis, and psoriasis.

The efficacy of TNF-R fragments and anti-TNF-α antibodies in treating TNF-α-mediated conditions demonstrates that reducing signaling through the TNF-α/TNF-R signaling pathway can be used effectively to treat TNF-α-mediated conditions. TNF-R fragments and anti-TNF-α antibodies, however, are expensive to produce. Moreover, these proteinaceous agents require intravenous administration.

There is, therefore, a need in the art for additional agents that reduce signaling through the TNF-α/TNF-R signaling pathway and that can be used for treatment of TNF-α-mediated conditions. Accordingly, the present inventors have discovered small molecule compounds that inhibit binding of TNF-α to TNF-R1 and reducing activity of the TNF-α/TNF-R1 signaling pathway. The compounds are useful for treatment of TNF-α mediated conditions.

SUMMARY

The present invention is directed to compounds that are inhibitors of TNF-R1, compositions thereof, and methods of using such compounds and compositions to treat conditions mediated by the TNF-R1/TNF-α signaling pathway.

In certain embodiments, the invention is directed towards compounds represented by formula (I), at least one stereoisomer thereof, or a salt, or a mixture thereof.

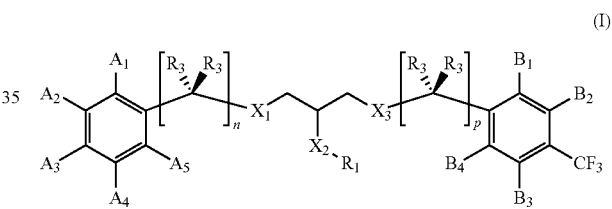

wherein, $A_1$-$A_5$ and $B_1$-$B_4$ are independently H, halo, hydroxyl, nitro, cyano, optionally substituted alkyl, optionally substituted alkoxy, —$(CH_2)_m$—S(O)$_q$R$_2$, —N(R$_1$)$_2$, —$(CH_2)_m$—X$_4$—C(X$_5$)—R$_2$, —$(CH_2)_m$—C(X$_5$)—X$_4$—R$_2$, —O—$(CH_2)_m$—X$_4$—C(X$_5$)—R$_2$, —O—$(CH_2)_m$—C(X$_5$)—X$_4$—R$_2$, —SO$_3$H, or —S(O)$_q$—R$_1$, or one or more pairs of $A_1$-$A_2$ or $A_2$-$A_3$ or $A_3$-$A_4$, or $A_4$-$A_5$ or $B_1$-$B_2$ or $B_3$-$B_4$, together with the respective carbons to which they are attached, form a $C_{5-8}$ alkyl, heteroalkyl, aryl, or heteroaryl ring, provided that at least one of $A_1$-$A_5$ moieties comprises —$(CH_2)_m$—X$_4$—C(X$_5$)—R$_2$;

$X_1$ is O, NR$_3$, —C(O)—O—, or S;

$X_2$, $X_4$, and $X_5$ are each independently 0, NR$_1$, or S;

$X_3$ is O, NR$_3$, —O—C(O)—, or S(O)$_q$;

m, n, and p and are each independently 0 or 1; q is 0, 1, or 2;

R$_1$ is independently in each case H, or optionally substituted aryl, heteroaryl, alkyl, or acyl;

R$_2$ is optionally substituted alkyl, aryl, or heteroaryl;

R$_3$ is independently in each case H, R$_1$, —OR$_1$, or when taken together with the other R$_3$ attached to the same carbon is =O.

In other embodiments, the invention is directed to compounds as described above, with the proviso the compound is not a compound of formula (II).

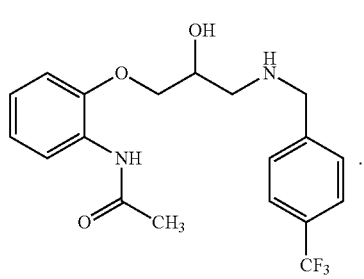

In other embodiments, the invention is directed to a compound represented by the formula:

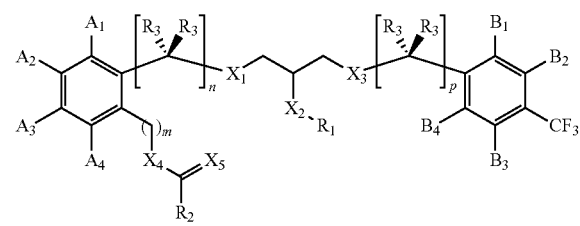

The invention includes those compounds more specifically directed toward a compound represented by the formula:

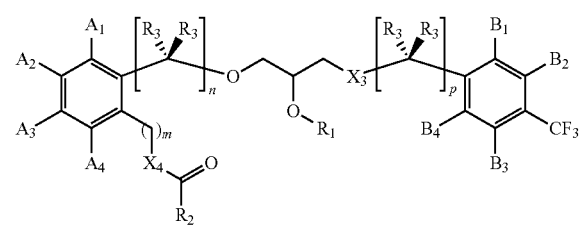

where $X_3$ is O or N—$R_1$, or even more specifically wherein $X_3$ is N—H, or when n=1:

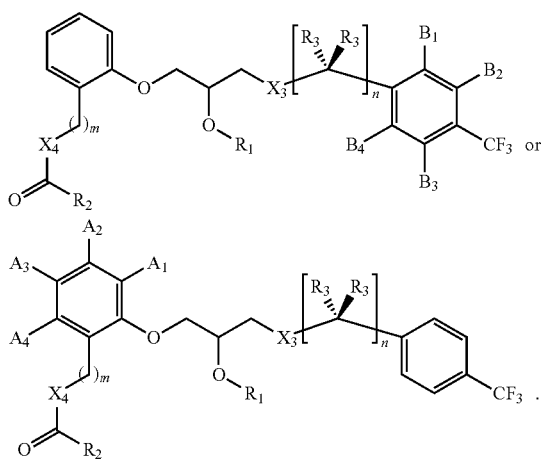

In other embodiments, n=1 and p=0, while in others, both n and p=0. Non-limiting exemplary structures include:

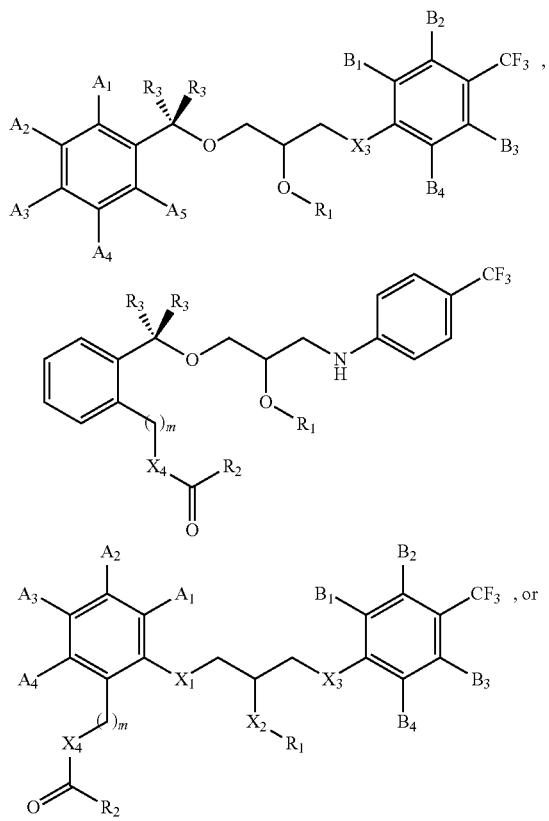

In another embodiment, the invention is directed to a compound having a structure:

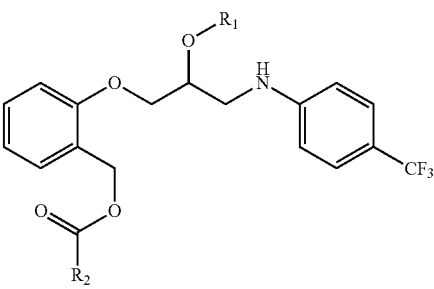

wherein $R_1$ and $R_2$ are each independently $C_{1-3}$ alkyl, more preferable either or both are methyl.

In certain embodiments, the invention is directed to one of the aforementioned compounds, including the compound of formula (II), or a compound different from the aforementioned compounds, that is capable of binding in a cavity of a tumor necrosis factor receptor (TNF-R), said cavity bounded by Cys-76, Arg-77, Asp-93, Cys-96, Arg-104, Asn-110, Phe-112, and Lys-132.

In other embodiments, the invention teaches that the aforementioned compounds inhibit at least 40% of TNFα induced cytolysis at a concentration of 50 micromolar and/or at least 60% of TNFα induced cytolysis at a concentration of 90 micromolar.

In other embodiments, the invention is directed to a pharmaceutical composition comprising a therapeutically effective amount of any of the aforementioned compounds and a pharmaceutically acceptable excipient.

In other embodiments, the invention is directed to methods of treatment of a TNF-α mediated condition, comprising administering an effective amount any of the aforementioned compounds or compositions to a patient in need of such treatment. In other embodiments, the invention is directed to methods of inhibiting tumor necrosis factor action, comprising administering an effective amount of any of the aforementioned compounds or compositions to a patient in need of such treatment. Preferred embodiments of the invention include methods of treating arthritis, inflammation, psoriasis, or an autoimmune condition comprising administering an effective amount of any of the aforementioned compounds or compositions to a patient in need of such treatment.

In yet other embodiments, the invention is directed to use of any of the aforementioned compounds or compositions in the manufacture of a medicament for the therapeutic and/or prophylactic treatment of an autoimmune condition, including conditions such as arthritis, inflammation, and psoriasis.

DETAILED DESCRIPTION OF ILLUSTRATIVE EMBODIMENTS

Figure 1:
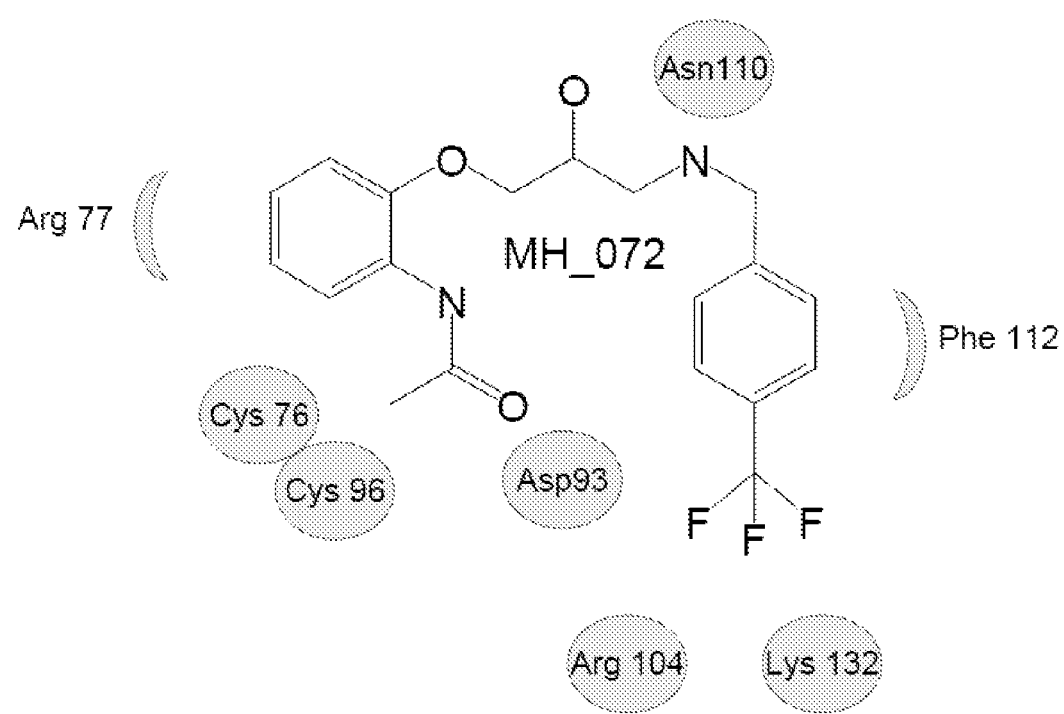
FIG. 1 illustrates one possible positioning of MH072 within a cavity of TNF-R bounded by Cys-76, Arg-77, Asp-93, Cys-96, Arg-104, Asn-110, Phe-112, and Lys-132 of SEQ ID No. 0001.

The present inventions are directed to the area of compounds and methods for inhibiting functions mediated by tumor necrosis factor. Such compounds and methods can also be used in treating diseases, disorders, and conditions in which tumor necrosis factor is a participant.

The present invention may be understood more readily by reference to the following detailed description taken in connection with the accompanying Figures and Examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the compounds and to the resulting pharmaceutical compositions and methods of manufacture and use.

In the present disclosure the singular forms "a," "an," and "the" include the plural reference, and reference to a particular numerical value includes at least that particular value, unless the context clearly indicates otherwise. Thus, for example, a reference to "a compound" is a reference to at least one of such compounds and equivalents thereof known to those skilled in the art, and so forth.

When values are expressed as approximations, by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. Where present, all ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

Generally terms are to be given their plain and ordinary meaning such as understood by those skilled in the art, in the context in which they arise. To avoid any ambiguity, however, several terms are described herein.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references that are provided throughout this document. The nomenclature used herein and the laboratory procedures in analytical chemistry, and organic synthetic chemistry described below are those well known and commonly employed in the art. Standard techniques, or modifications thereof, are used for chemical syntheses and chemical analyses.

Whenever a group of this invention is described as being "optionally substituted" that group may be unsubstituted or substituted with one or more of the substituents described for that group. Likewise, when a group is described as being "unsubstituted or substituted," if substituted, the substituent may be selected from the same group of substituents. Unless otherwise indicated, when a substituent is deemed to be "optionally substituted," or "substituted" it is meant that the substituent is a group that may be substituted with one or more group(s) individually and independently selected.

Each of the following terms (e.g., "alkyl," "heteroalkyl," "acyl," "alkoxy," "aryl," and "heteroaryl") include both substituted and unsubstituted forms of the indicated group, unless indicated otherwise. Preferred substituents for each type of group are provided below.

The term "alkyl," by itself or as part of another substituent, means, unless otherwise stated, a straight or branched chain, or cyclic hydrocarbon group (cycloalkyl), or combination thereof, which may be fully saturated, mono- or polyunsaturated and can include di- and multivalent radicals, and can have a number of carbon atoms optionally designated (e.g., $C_{1-10}$ means one to ten carbons). Examples of saturated hydrocarbon groups include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotonyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl". Alkyl groups include, for example, $C_{1-6}$ unsubstituted alkyl, $C_{3-7}$ unsubstituted cycloalkyl, trifluoromethyl, chloromethyl, and hydroxymethyl.

An alkyl group of this invention may be substituted or unsubstituted. When substituted, the substituent group(s) may be one or more group(s) independently selected from cycloalkyl, aryl, heteroaryl, heteroalicyclyl, hydroxy, alkoxy, aryloxy, mercapto, alkylthio, arylthio, cyano, halo, oxo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, amino or substituted amino, protected hydroxyl, protected amino, protected carboxy and protected amido groups.

Substituents for the alkyl groups (including those groups often referred to as heteroalkyl, alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such group. R', R", R'" and R"" each preferably independently refer to hydrogen, substituted or unsubstituted alkyl including substituted or unsubstituted heteroalkyl, and substituted or unsubstituted aryl, e.g., aryl substituted with 1-3 halogens. When a compound of the invention includes more than one R group, for example, each of the R groups is independently selected as are each of the R', R", R'" and R"" groups when more than one of these groups is present.

As used herein, "alkenyl" refers to an alkyl group that contains in the straight or branched hydrocarbon chain one or more double bonds. Examples of alkenyl groups include, without limitation, vinyl (CH$_2$=CH—), allyl (CH$_3$CH=CH$_2$—), 1-propenyl, 2-propenyl, 1-butenyl, 2-butenyl; 1-pentenyl, 2-pentenyl, 3-pentenyl, 4-pentenyl, 3-methyl-1-butenyl, and the various isomers of hexenyl, heptenyl, octenyl, nonenyl, decenyl undecenyl and dodecenyl.

An alkenyl group of this invention may be unsubstituted or substituted. When substituted, the substituent(s) may be selected from the same groups disclosed above with regard to alkyl group substitution.

As used herein, "alkynyl" refers to an alkyl group that contains in the straight or branched hydrocarbon chain one or more triple bonds.

An alkynyl group of this invention may be unsubstituted or substituted. When substituted, the substituent(s) may be selected from the same groups disclosed above with regard to alkyl group substitution.

The term "alkylene" refers to an alkyl group, as defined here, which is a biradical and is connected to two other moieties. Thus, methylene (—CH$_2$—), ethylene (—CH$_2$CH$_2$—), propylene (—CH$_2$CH$_2$CH$_2$—), isopropylene (—CH$_2$—CH(CH$_3$)—), and isobutylene (—CH$_2$—CH(CH$_3$)—CH$_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "acyl" refers to an "RC(=O)—." An acyl group may contain an alkyl or aryl moiety, in which case it may be referred to as a carboxyalkyl or carboxyaryl group, respectively. Examples of acyl groups include, without limitation, formyl, acetyl, propionyl, butyryl, pentanoyl, pivaloyl, hexanoyl, heptanoyl, octanoyl, nonanoyl, decanoyl, undecanoyl, dodecanoyl and benzoyl. Presently preferred acyl groups are acetyl and benzoyl.

An acyl group of this invention may be unsubstituted or substituted. When substituted, the substituent(s) may be selected from the same groups disclosed above with regard to alkyl group substitution.

The term "alkoxy" is used in its conventional sense, and refers to those alkyl groups attached to the remainder of the molecule via an oxygen atom. Alkoxy groups include, but are not limited to methoxy, ethoxy, propoxy, trifluoromethoxy and difluoromethoxy.

An "amide" is a chemical moiety with formula —(R)$_n$—C(O)NHR' or —(R)$_n$—NHC(O)R', where n is the number of alkylene carbons from 0-1, R and R' are independently selected from the group consisting of alkyl, cycloalkyl, aryl, heteroaryl (bonded through a ring carbon) and heteroalicyclic (bonded through a ring carbon). An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, Protective Groups in Organic Synthesis, 3.sup.rd Ed., John Wiley & Sons, New York, N.Y., 1999, which is incorporated herein in its entirety.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system. Aryl-containing groups include, but are not limited to, phenyl, phenoxy, phenoxycarbonyl, benzoyl, benzyl, and benzyloxy.

Aryl-containing groups include, but are not limited to, phenyl, phenoxy, phenoxycarbonyl, benzoyl, benzyl, and benzyloxy.

Similar to the substituents described for alkyl groups, the aryl substituents are generally referred to as "aryl substituents" and are varied and selected from, for example: halogen, —OR', =O, =NR', —N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN, —NO$_2$, —R', and —N$_3$, in a number ranging from zero to the total number of open valences on the aromatic ring system; and where R', R", R''' and R'''' are preferably independently selected from hydrogen, substituted or unsubstituted alkyl including substituted or unsubstituted heteroalkyl, and unsubstituted aryl. When a compound of the invention includes more than one R group, for example, each of the R groups is independently selected as are each of the R', R", R''' and R'''' groups when more than one of these groups is present.

The term "aryloxy" is used in its conventional sense, and refers to those aryl groups attached to the remainder of the molecule via an oxygen atom.

The term "cycloalkyl", by itself or in combination with other terms, represents, unless otherwise stated, cyclic versions of substituted or unsubstituted "alkyl" and substituted or unsubstituted "heteroalkyl" ("heterocycloalkyl"). For heterocycloalkyl, a heteroatom can occupy the position at which the heterocycle is attached to the remainder of the molecule. The heteroatoms and carbon atoms of the cyclic structures are optionally oxidized or, in the case of N, quaternized. Cycloalkyl groups of this invention may range from $C_3$ to $C_8$. A cycloalkyl group may be unsubstituted or substituted. If substituted, the substituent(s) may be selected from those indicated above with regard to substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heteroalicyclic.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

As used herein, an "ether" refers to an "—C—O—C—" group wherein either or both carbons may independently be part of an alkyl, alkenyl, alkynyl, aryl, heteroaryl or heteroalicyclyl group. A "halogenated ether" refers to an ether in which the groups to either side of the oxygen are both alkyl substituted with halogen.

The terms "halo" or "halogen," by themselves or as part of another substituent, mean, unless otherwise stated, a fluorine, chlorine, bromine, or iodine atom. Preferred halogens are chloro and fluoro.

As used herein, the term "heteroatom" includes oxygen (O), nitrogen (N), sulfur (S), boron (B) and silicon (Si).

The term "heteroalkyl," by itself or in combination with another term, means, unless otherwise stated, a stable straight or branched chain, or cyclic hydrocarbon group, or combinations thereof, consisting of a number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

As used herein, "heteroaryl" refers to a ring that contains one or more heteroatoms selected from the group consisting of nitrogen, oxygen and sulfur in the ring and that has a fully delocalized pi-electron system. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, but are not limited to, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine.

As used herein, "heteroarylalkyl" and "heteroalicyclylalkyl" refer to a heteroaryl or a heteroalicyclyl group covalently bonded to an alkyl group, as defined herein As used herein, "heterocycloalkyl," "heteroalicyclic," or "heteroalicyclyl" refers to a ring having in the ring system one or more heteroatoms independently selected from nitrogen, oxygen and sulfur. The ring may also contain one or more double bonds provided that they do not form a fully delocalized pi-electron system in the rings. Heteroalicyclyl groups of this invention may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethanesulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heteroalicyclic.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

As used herein, "phenylalkyl" refers to a phenyl ring covalently bonded to an alkyl group as defined herein. Examples, without limitation, of phenylalkyl groups include, without limitation, benzyl, 2-phenylethyl, 1-phenylpropyl, 4-phenylhexyl, 3-phenylamyl and 3-phenyl-2-methylpropyl. Presently preferred phenylalkyl groups are those wherein the phenyl group is covalently bonded to one of the presently preferred alkyl groups. A phenyl alkyl group of this invention may be unsubstituted or substituted. Examples of substituted phenylalkyl groups include, without limitation, 2-phenyl-1-chloroethyl, 2-(4-methoxyphenyl) ethyl, 4-(2,6-dihydroxy phenyl)hexyl, 2-(5-cyano-3-methoxyphenyl)pentyl, 3-(2,6-dimethylphenyl)propyl, 4-chloro-3-aminobenzyl, 6-(4-methoxyphenyl)-3-carboxy (n-hexyl), 5-(4-aminomethylphenyl)-3-(aminomethyl)pentyl and 5-phenyl-3-oxo-pent-1-yl.

As used herein, "phenyl" refers to a 6-member aryl group. A phenyl group may be unsubstituted or substituted. When substituted the substituent(s) is/are one or more, preferably one or two, group(s) independently selected from the group consisting of halogen, hydroxy, protected hydroxy, cyano, nitro, alkyl, alkoxy, acyl, acyloxy, carboxy, protected carboxy, carboxymethyl, protected carboxymethyl, hydroxymethyl, protected hydroxymethyl, amino or substituted amino, carboxamide, protected carboxamide, N-alkylcarboxamide, protected N-alkylcarboxamide, N,N-dialkylcarboxamide, trifluoromethyl, N-alkylsulfonylamino, N-(phenylsulfonyl) amino and phenyl (resulting in the formation of a biphenyl group).

As used herein, "phenylalkoxy" refers to a "phenylalkyl-O-" group with "phenyl" and "alkyl" as defined herein. A phenylalkoxy group of this invention may be substituted or unsubstituted on the phenyl ring, in the alkyl group or both.

As used herein, "amino protecting group" refers to a group commonly employed to keep (i.e., to "block" or "protect") an amino group from reacting with a reagent while it reacts with an intended target functional group of a molecule.

Examples of amino protecting groups include, without limitation, formyl ("For"), trityl, phthalimido, trichloroacetyl, chloroacetyl, bromoacetyl, iodoacetyl groups, t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxy-carbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropyl-methoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, -2,4,5,-tetramethylbenzyloxycarbonyl ("Tmz"), 4-methoxybenzyloxy-carbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyl-oxycarbonyl, 4-bromobenzyloxycarbonyl, 3-bromobenzyloxycarbonyl, 4-nitrobenzyloxy-carbonyl, 4-cyanobenzyloxycarbonyl, 4-(decyloxy) benzyloxycarbonyl, benzoylmethylsulfonyl, dithiasuccinoyl ("Dts"),2-(nitro) phenylsulfenyl ("Nps"), and diphenyl-phosphine oxide. The species of amino-protecting group employed is not critical so long as the derivatized amino group is stable to the conditions of the subsequent reaction(s) and can be removed at the appropriate point without disrupting the remainder of the molecule. Presently preferred amino-protecting groups are Boc, Cbz and Fmoc. Descriptions of these and other amino-protecting groups may be found in T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984.

As used herein, the term "carboxy protecting group" refers to a labile ester commonly used to block or protect a carboxylic acid while reactions are carried out on other functional groups on the compound. Examples of carboxy protecting groups include, without limitation, t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, -(trimethylsilyl)ethyl, -(di(n-butyl)methylsilyl)ethyl, p-toluenesulfonylethyl, 4-nitrobenzylsulfonylethyl, allyl, cinnamyl, and 1-(trimethylsilylmethyl)-propenyl. The ester employed is not critical so long as it is stable to the conditions of subsequent reaction(s) and can be removed at the appropriate point without disrupting the remainder of the molecule. Further examples of carboxy-protecting groups are found in E. Haslam, *Protective Groups in Organic Chemistry*," J. G. W. McOmie, Ed., Plenum Press, New York, N.Y., 1973, Chapter 5, and T. W. Greene and P. G. M. Wuts, "*Protective Groups in Organic Synthesis,*" 2nd ed., John Wiley and Sons, New York, N.Y., 1991, Chapter 5.

As used herein, a "hydroxyl protecting group" refers to a readily cleavable group that replaces the hydrogen of the hydroxyl group, such as, without limitation, tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, and 2,2,2-trichloroethoxycarbonyl. The species of hydroxyl protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

As used herein, "alkylthio" refers to an "alkyl-S—" group, with alkyl as defined above. Examples of alkylthio group include, without limitation, methylthio, ethylthio, n-propylthio, isopropylthio, n-butylthio and t-butylthio.

As used herein, "alkylsulfinyl" refers to an "alkyl-SO—" group, with alkyl as defined above. Examples of alkylsulfinyl groups include, without limitation, methylsulfinyl, ethylsulfinyl, n-propylsulfinyl, isopropylsulfinyl, n-butylsulfinyl and sec-butylsulfinyl.

By "perhaloalkyl" it is meant an alkyl moiety where all of the hydrogen atoms normally present on the alkyl are replaced by a halogen. Thus, for example, a perchloroalkyl is an alkyl moiety where all of the carbon atoms not connected to the rest of the molecule are connected to chlorine atoms.

When two substituents taken together along with the carbon atoms to which they are attached form a five- or six-membered optionally substituted carbocyclic ring or optionally substituted heterocyclic ring, or form a six-membered optionally substituted aryl, optionally substituted heteroaryl, it is meant that the following structure:

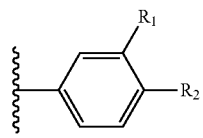

can be representative of, for example, the following structures:

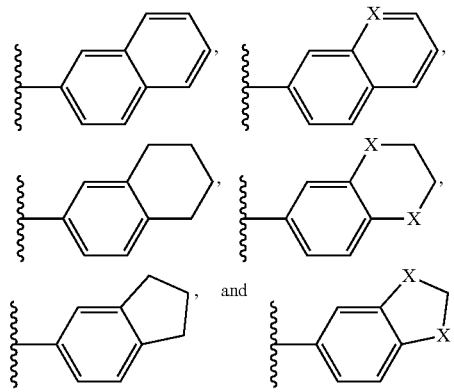

where X is a heteroatom.

Throughout the present disclosure, when a particular compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R, R and S, S isomers, compositions comprising the racemic mixture of R, S and S, R isomers, compositions comprising the R, R enantiomer substantially free of the other diastereomers, compositions comprising the S, S enantiomer substantially free of the other diastereomers, compositions comprising the R, S enantiomer substantially free of the other diastereomers, and compositions comprising the S, R enantiomer substantially free of the other diastereomers.

The term "pharmaceutically acceptable salt" means those salts of compounds of the invention that are safe and effective for use in a subject and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 J. Pharm. Sci 1-19 (1977), incorporated herein by reference.

Compounds

One embodiment of a suitable compound for a pharmaceutical composition is represented by formula (I), or is a pharmaceutically acceptable salt thereof:

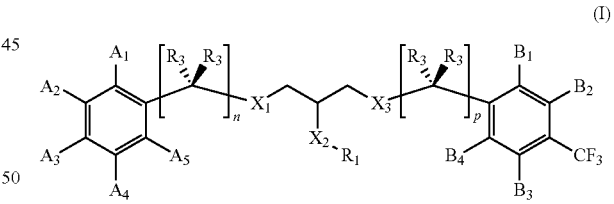

wherein, $A_1$-$A_5$ and $B_1$-$B_4$ are independently H, halo, hydroxyl, nitro, cyano, optionally substituted alkyl, optionally substituted alkoxy, —$(CH_2)_m$—S(O)$_q$$R_2$, —$N(R_1)_2$, —$(CH_2)_m$—$X_4$—C($X_5$)—$R_2$, —$(CH_2)_m$—C($X_5$)—$X_4$—$R_2$, —O—$(CH_2)_m$—$X_4$—C($X_5$)—$R_2$, —O—$(CH_2)_m$—C($X_5$)—$X_4$—$R_2$, —$SO_3H$, or —S(O)$_q$—$R_1$, or one or more pairs of $A_1$-$A_2$ or $A_2$-$A_3$ or $A_3$-$A_4$, or $A_4$-$A_5$ or $B_1$-$B_2$ or $B_3$-$B_4$, together with the respective carbons to which they are attached, form a $C_{5-8}$ alkyl, heteroalkyl, aryl, or heteroaryl ring, provided that at least one of $A_1$-$A_5$ moieties comprises —$(CH_2)_m$—$X_4$—C($X_5$)—$R_2$;

$X_1$ is O, $NR_3$, —C(O)—O—, or S;

$X_2$, $X_4$, and $X_5$ are each independently O, $NR_1$, or S;

$X_3$ is O, $NR_3$, —O—C(O)—, or S(O)$_q$;

m, n, and p and are each independently 0 or 1; q is 0, 1, or 2;

R$_1$ is independently in each case H, or optionally substituted aryl, heteroaryl, alkyl, or acyl;

R$_2$ is optionally substituted alkyl, aryl, or heteroaryl;

R$_3$ is independently in each case H, R$_1$, —OR', or when taken together with the other R$_3$ attached to the same carbon is =O.

The various substituents can be selected in view of factors such as, for example, absorption, activity, affinity, distribution, excretion, metabolism, pharmacokinetic, solubility, toxicological and other properties conducive to their use as pharmaceuticals.

Depicting the general structure even more broadly as:

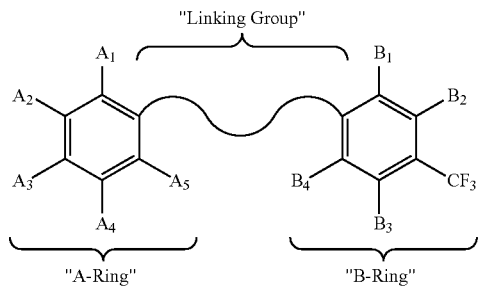

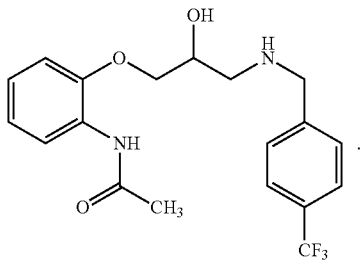

(II)

In other embodiments, the compound is represented by formula (I), or is a pharmaceutically acceptable salt thereof, wherein the compound is capable of binding in a cavity of a tumor necrosis factor receptor (TNF-R), said cavity bounded by Cys-76, Arg-77, Asp-93, Cys-96, Arg-104, Asn-110, Phe-112, and Lys-132. The structure sequence of TNF-R has previously been disclosed in WO2006/083970, which is incorporated by reference herein. For the sake of completeness, the amino acid sequence for this protein (SEQ ID No. 0001) is described as:

```
Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20              25                  30

Cys His Lys Gly Thr Tyr Leu Tyr Asn Asp Cys Pro Gly Pro Gly Gln
            35              40                  45

Asp Thr Asp Cys Arg Glu Cys Glu Ser Gly Ser Phe Thr Ala Ser Glu
        50              55              60

Asn His Leu Arg His Cys Leu Ser Cys Ser Lys Cys Arg Lys Glu Met
65                  70              75                  80

Gly Gln Val Glu Ile Ser Ser Cys Thr Val Asp Arg Asp Thr Val Cys
                85              90                  95

Gly Cys Arg Lys Asn Gln Tyr Arg His Tyr Trp Ser Glu Asn Leu Phe
            100             105                 110

Gln Cys Phe Asn Cys Ser Leu Cys Leu Asn Gly Thr Val His Leu Ser
            115             120             125

Cys Gln Glu Lys Gln Asn Thr Val Cys Thr Cys His Ala Gly Phe Phe
        130             135             140

Leu Arg Glu Asn Glu Cys Val Ser Cys Ser Asn Cys Lys Lys Ser Leu
145                 150             155                 160

Glu Cys Thr Lys Leu Cys Leu Pro Gln Ile Glu Asn
            165             170
``` the invention teaches that, in certain embodiments, the A-Ring and B-Ring are spatially positioned relative to one another such that the linking group comprises 5-8 carbon or heteroatoms.

In other embodiments, the invention is directed to compounds as described above, with the proviso the compound is not a compound of formula (II).

In another embodiment, the compound is represented by formula (I), or is a pharmaceutically acceptable salt thereof, wherein the optionally substituted alkyl, acyl, and alkoxy groups comprise C$_{1-6}$ moieties, preferably C$_{1-3}$ moieties, the C$_{1-3}$ moieties including methyl, ethyl, propyl, and isopropyl, more preferably methyl. In other embodiments, the substituents on these alkyl, acyl, and alkoxy groups comprise fluorine.

The positioning of the at least one —(CH$_2$)$_m$—X$_4$—C(X$_5$)—R$_2$ can be in any of the A$_1$-A$_5$ positions, That is, in various embodiments, each one of A1, A$_2$, A$_3$, A$_4$, and A$_5$ is —(CH$_2$)$_m$—X$_4$—C(X$_5$)—R$_2$. In certain other embodiments, one or more of the remaining A$_1$-A$_5$ positions are hydrogen. Exemplary structures corresponding to these embodiments include:

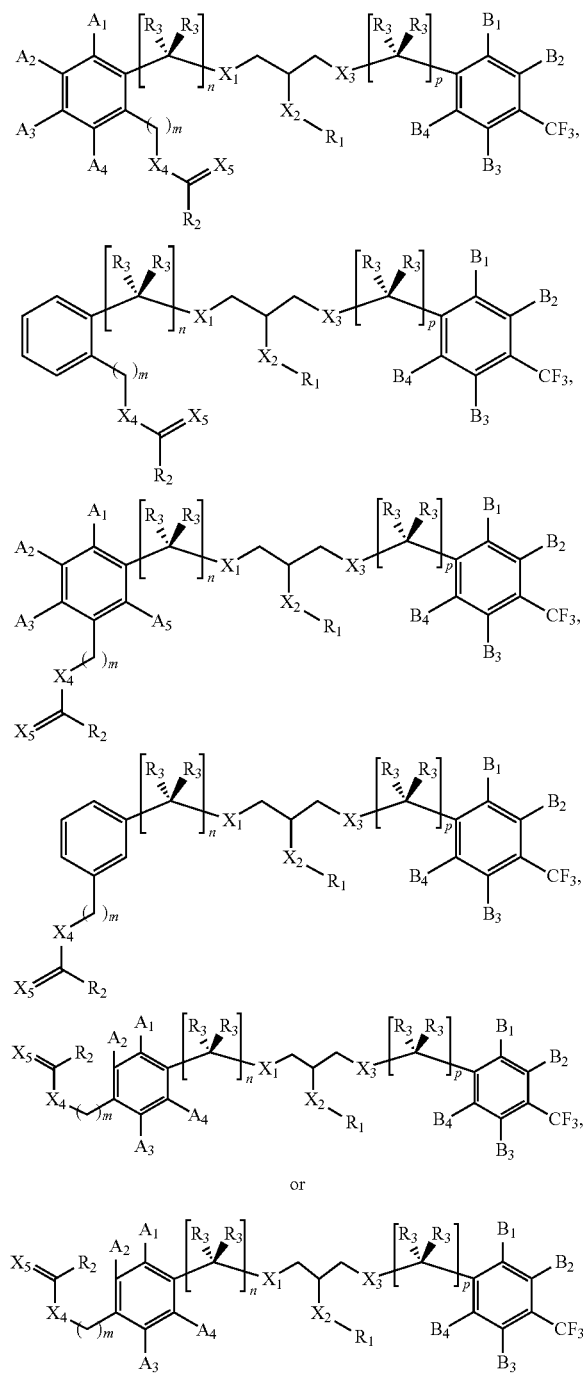

In certain other embodiments, X$_4$ is S. In others, X$_4$ is O or NH. In other embodiments, X$_5$ is O. In each case, m can be either 0 or 1. Exemplary structures corresponding to some of these embodiments include:

-continued

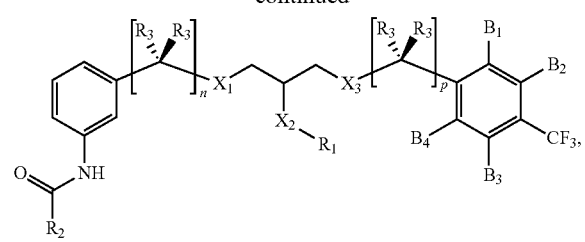

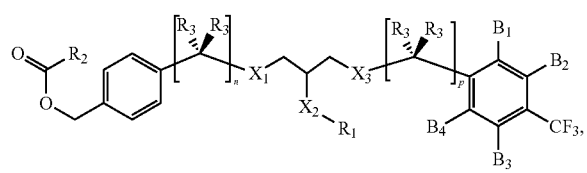

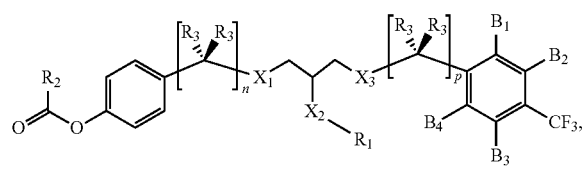

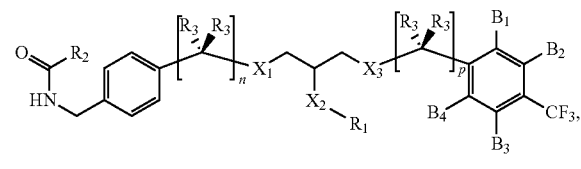

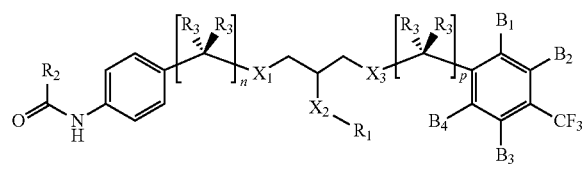

or

In related embodiments, $R_2$ is optionally substituted $C_{1-6}$ alkyl, preferably $C_{1-3}$ alkyl, including methyl, ethyl, propyl, and isopropyl. $R_2$ can also be optionally substituted alkoxyl or amino, thereby providing the corresponding alkoxycarbonyl or carbamate. The invention therefore teaches that $R_2$ can be methyl corresponding to the following exemplary structures:

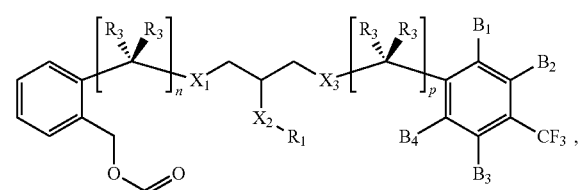

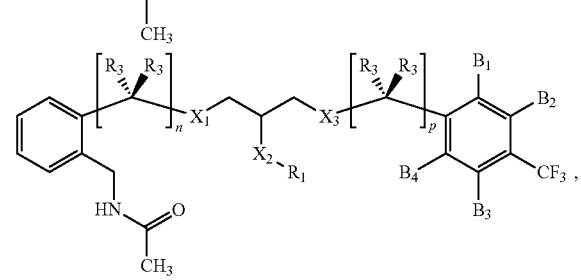

-continued

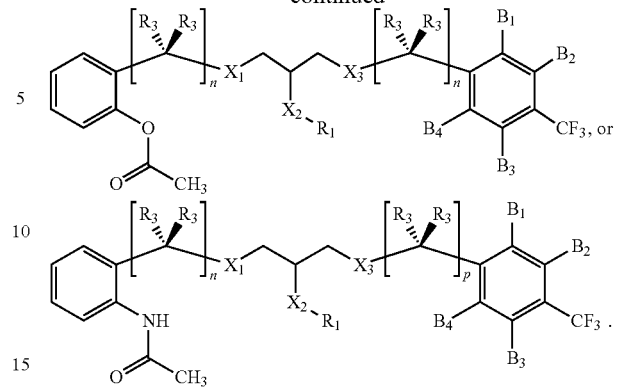

The invention provides compound of formula (I) wherein $X_1$ and $X_2$ are both O, as in:

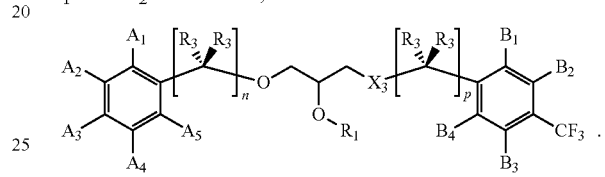

Certain embodiments of the compound of formula (I) also comprise those structures wherein $X_1$, $X_2$, and $X_5$ are all O; i.e.,

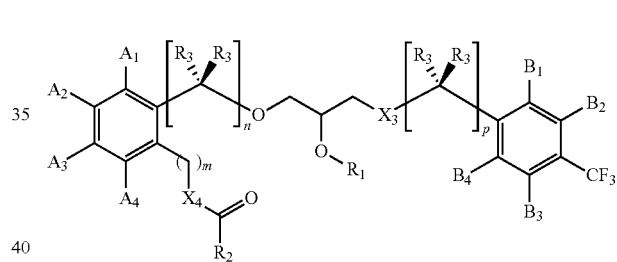

or

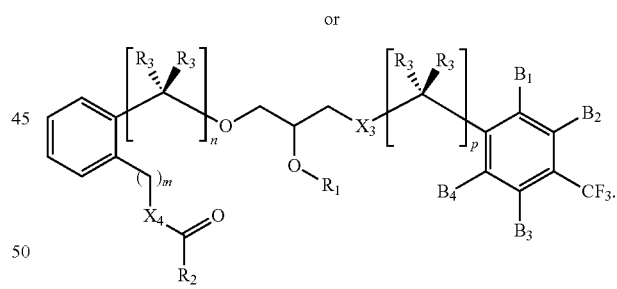

Other embodiments provide these compounds of formula (I) wherein $X_3$ is O, NH, —O—C(O)—. For example,

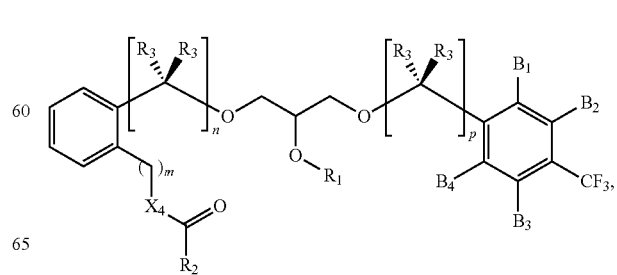

21
-continued
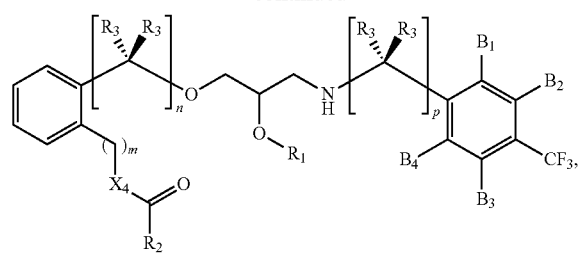
or
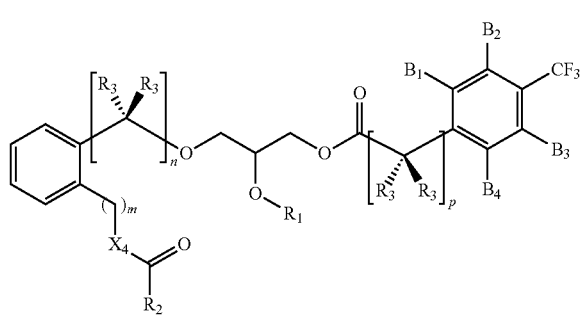
Likewise, particular embodiments wherein $X_4$ is O or NH, provides structures exemplified by the isomers according to
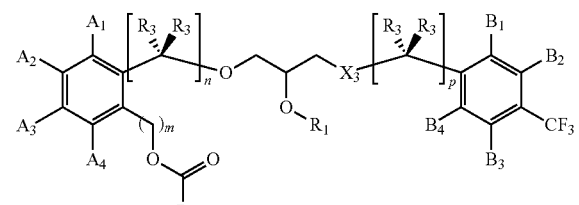
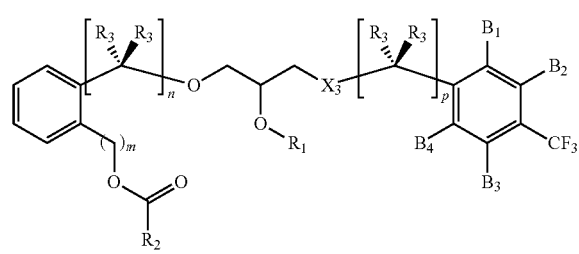
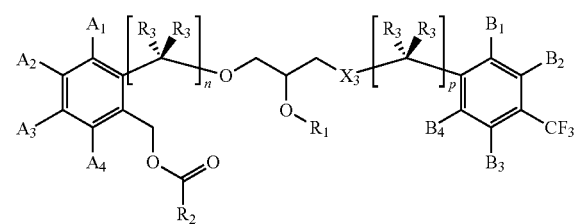
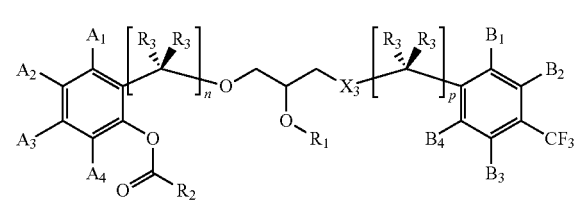
22
-continued
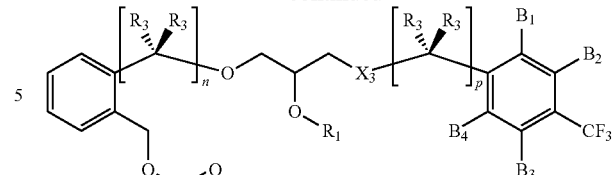
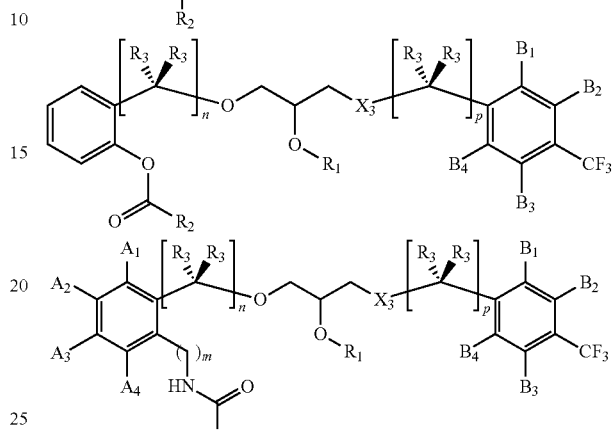
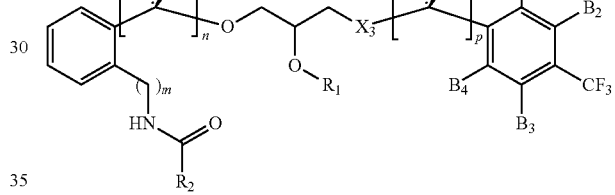
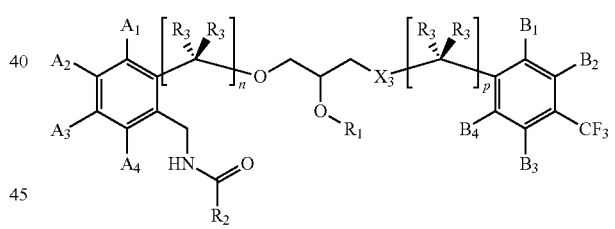
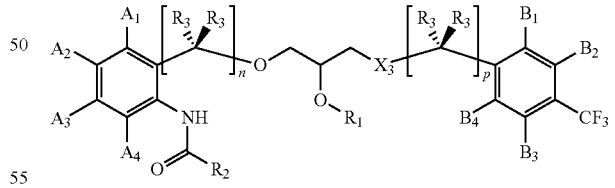
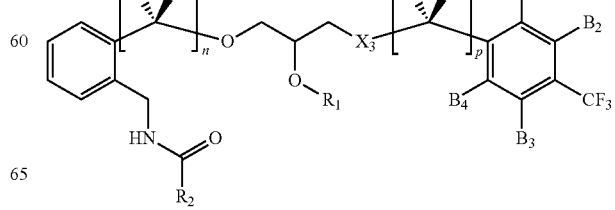

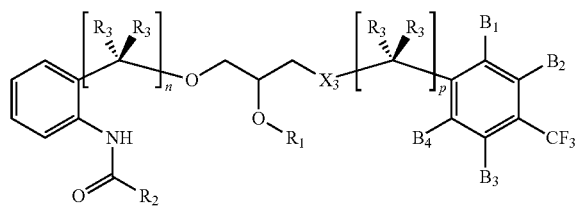

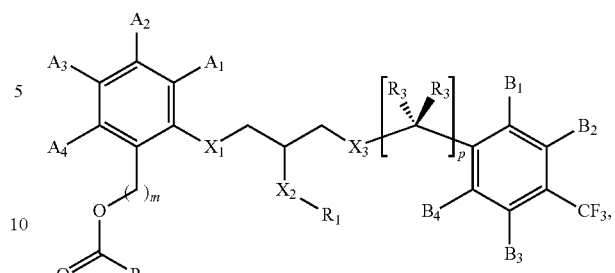

While these structures (and those that follow) show the $A_1$-$A_5$ ring as an ortho isomer (i.e., corresponding to the —(CH$_2$)—X$_4$—C(O)—R$_2$ moiety in the $A_1$ or $A_5$ position), is should be appreciated that a meta isomer (i.e., corresponding to the —(CH$_2$)—X$_4$—C(O)—R$_2$ moiety in the $A_2$ or $A_4$ position) and a para isomer (i.e., corresponding to the —(CH$_2$)—X$_4$—C(O)—R$_2$ moiety in the $A_3$ position) are also considered within the scope of this invention.

As one skilled in the art will appreciate, the compound of formula (I) may also comprise a compound wherein n=0, shown generally as

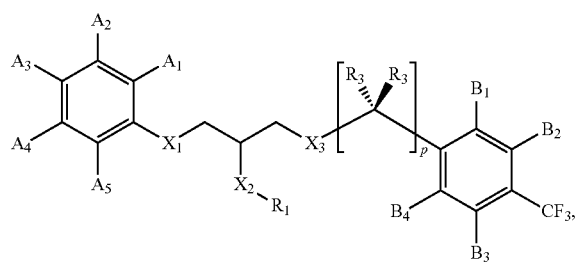

but also described in terms of the following non-limiting examples:

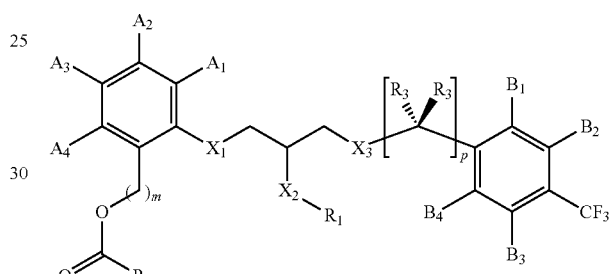

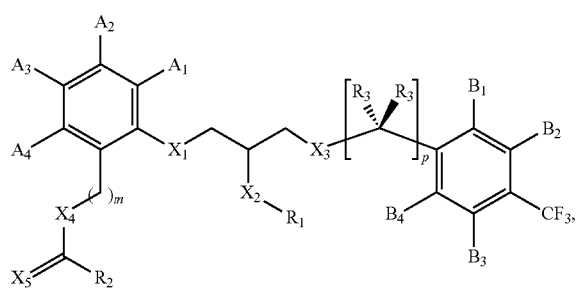

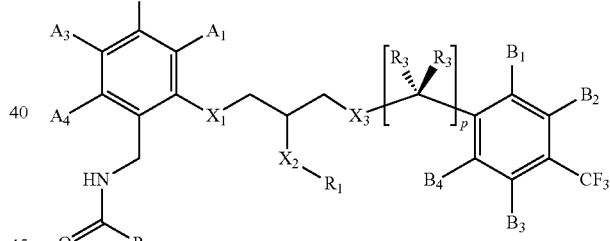

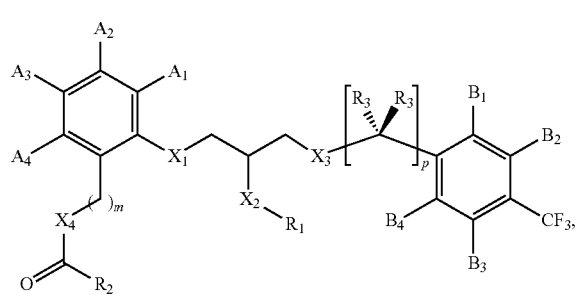

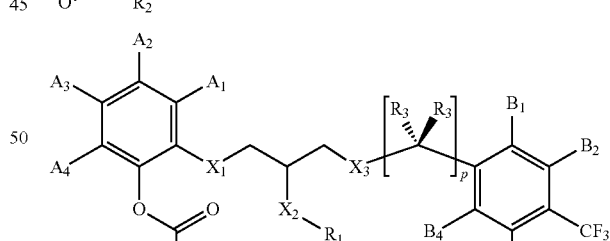

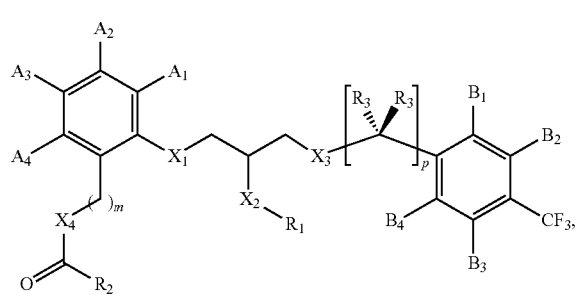

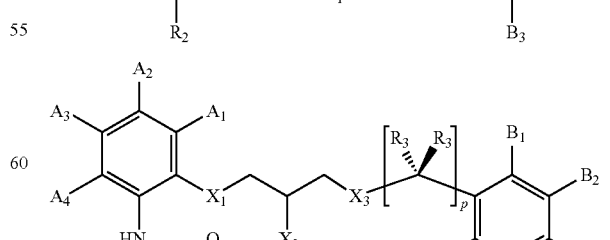

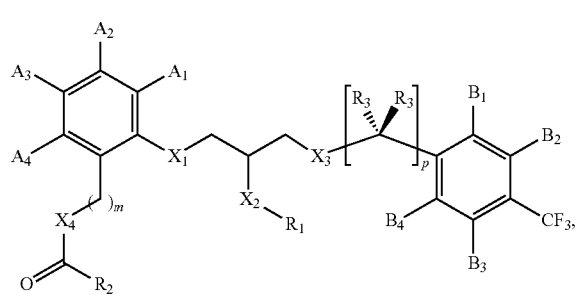

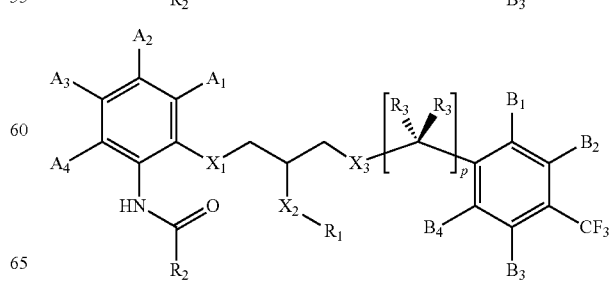

-continued
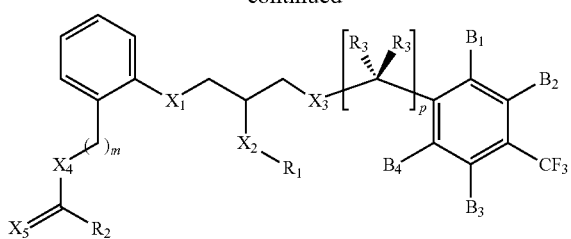
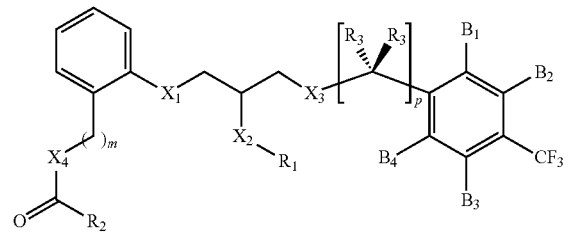
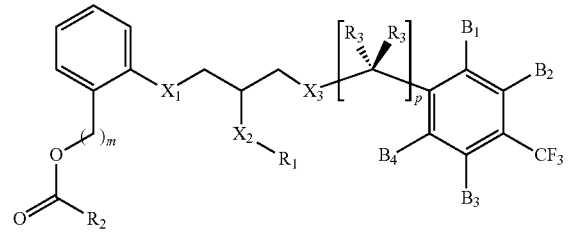
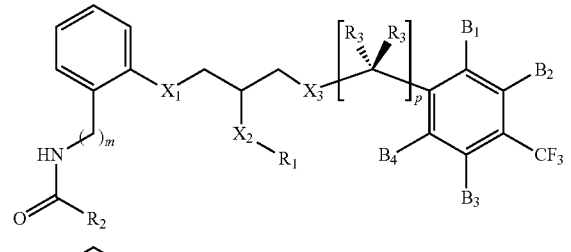
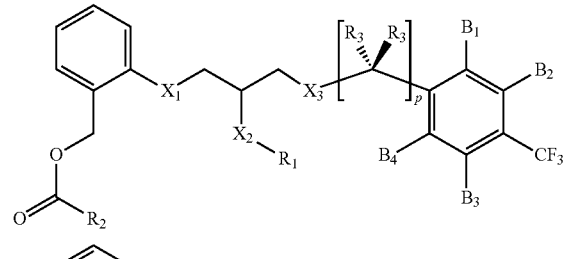
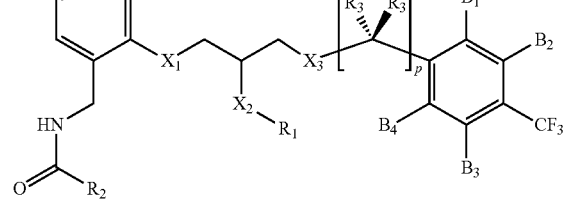
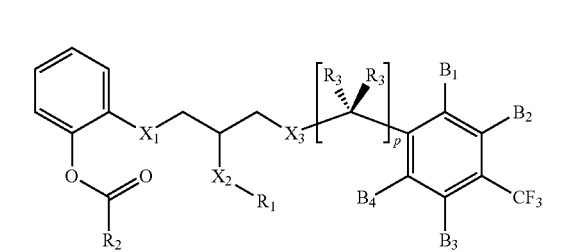
-continued
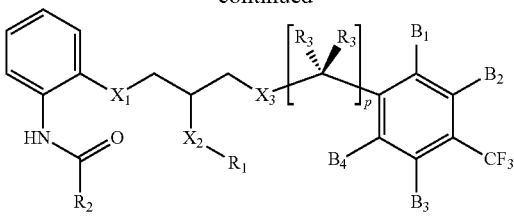
When $X_1$ and $X_2$ are both O, exemplary structures include:
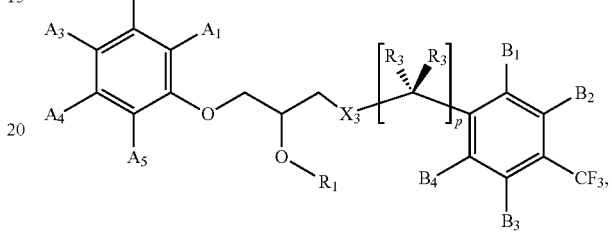
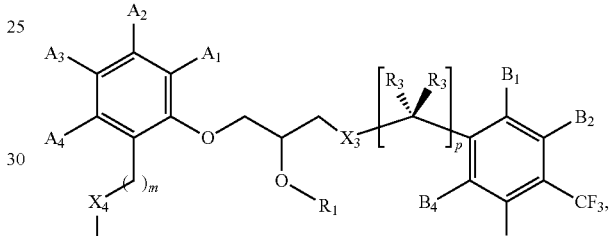
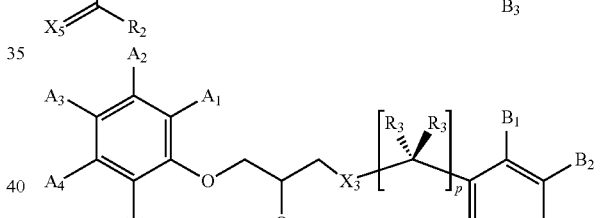
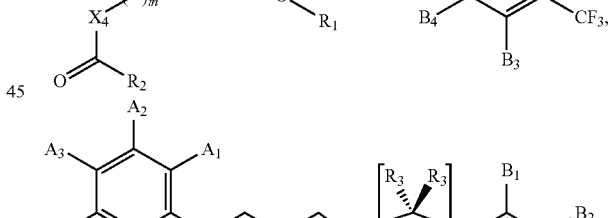
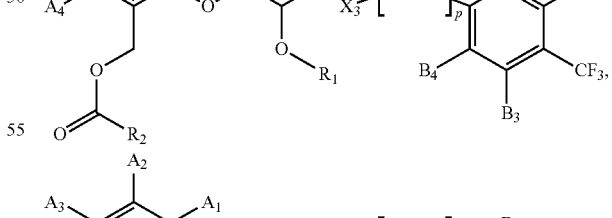
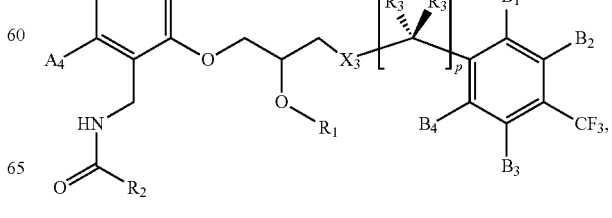

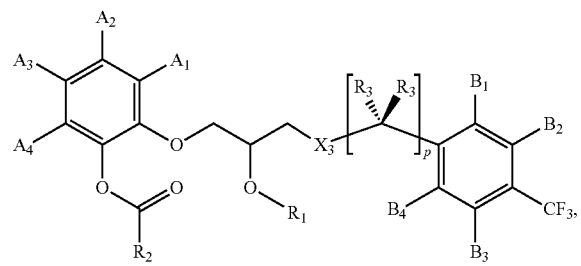
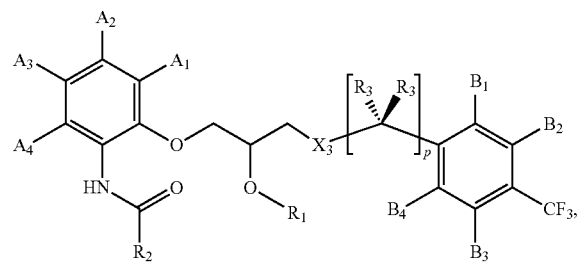
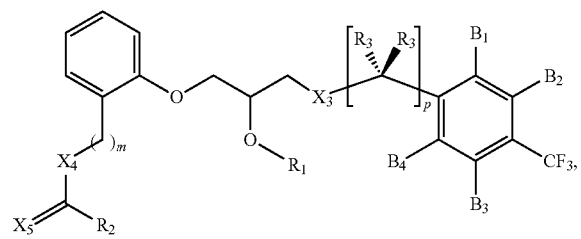
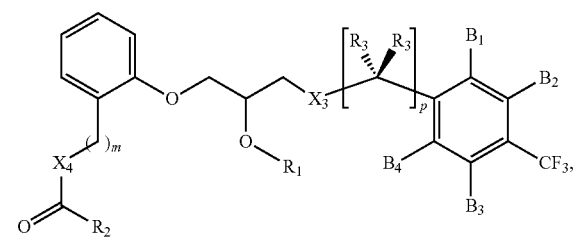
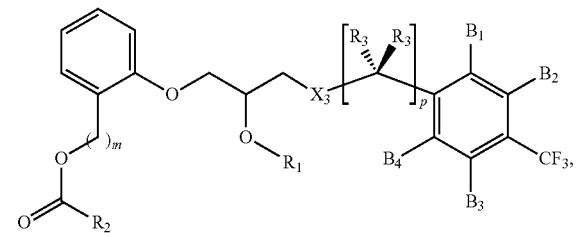
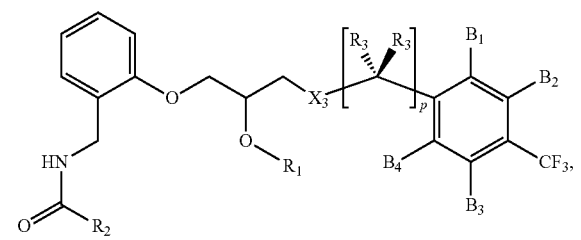
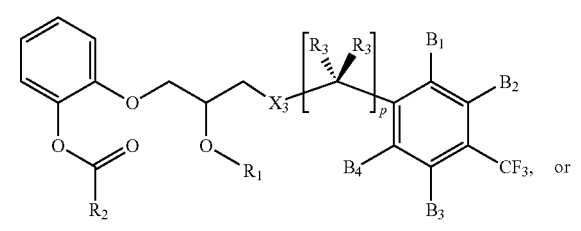
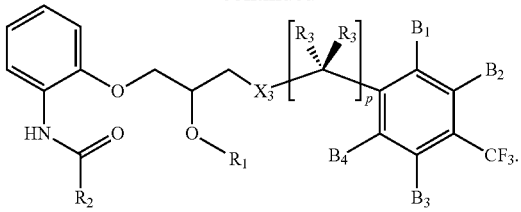
Other exemplary structures of this general class include those wherein either both $R_3$ are H, $X_3$=NH, or both:
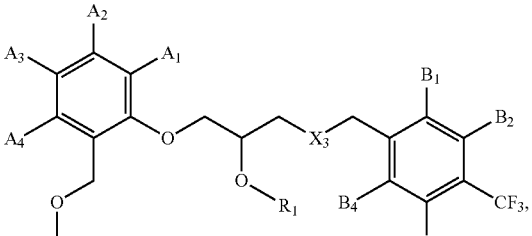
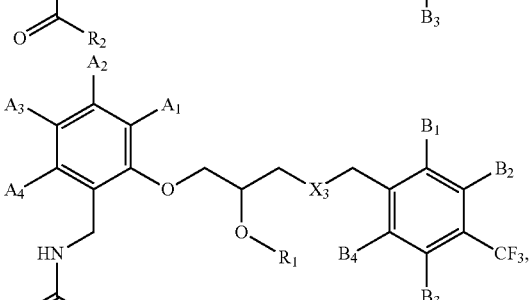
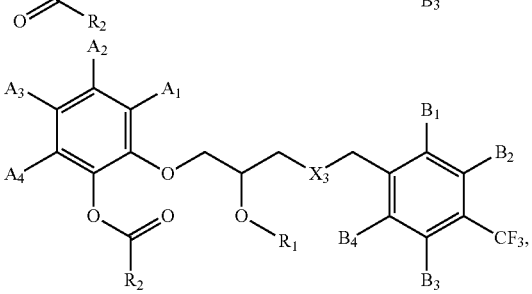
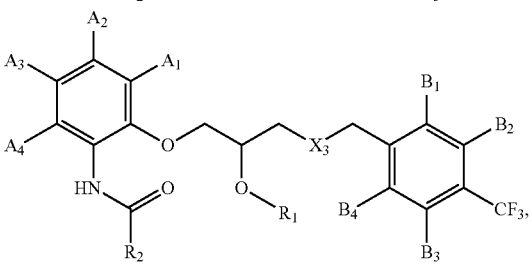
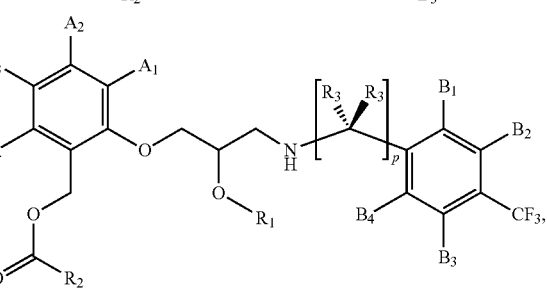

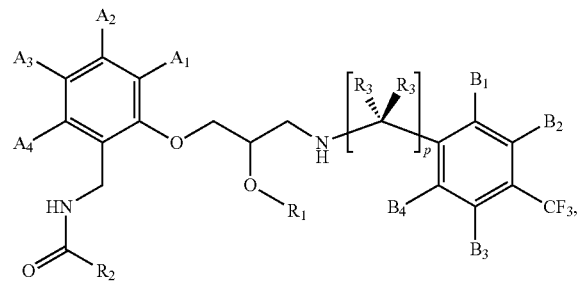
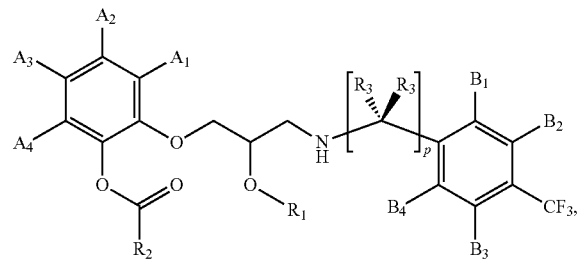
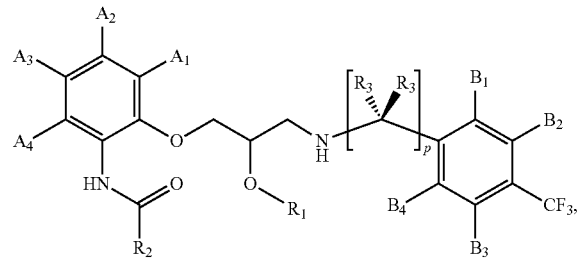
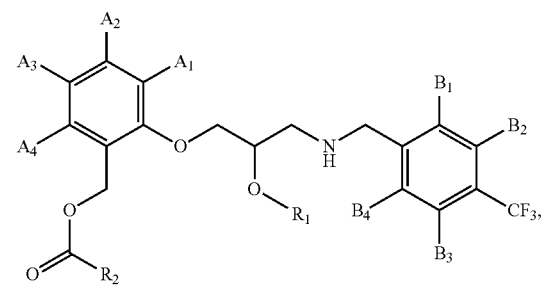
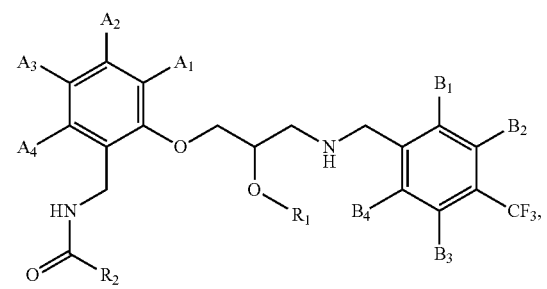
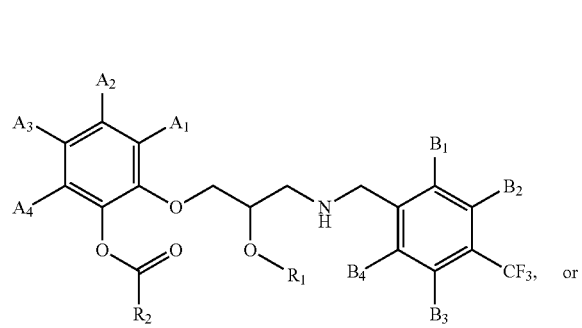
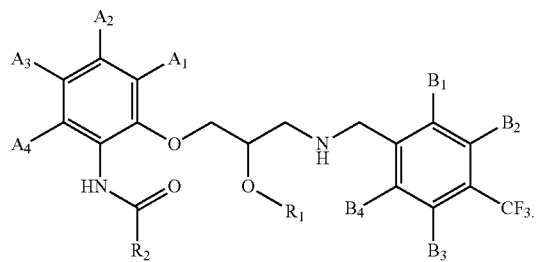
Similar structures include the structures comprising the various positional isomers of the $A_1$-$A_5$ ring (as described above), wherein the remaining $A_1$-$A_5$ and $B_1$-$B_4$ are all H.
Similarly, when p=0, non-limiting exemplary structures include:
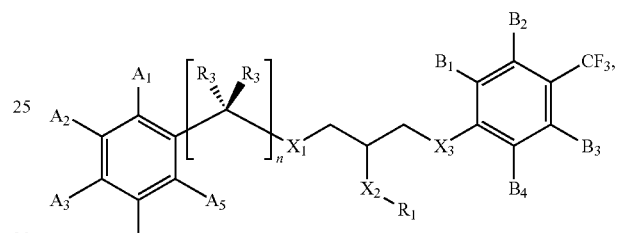
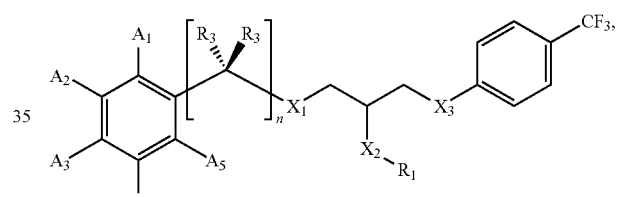
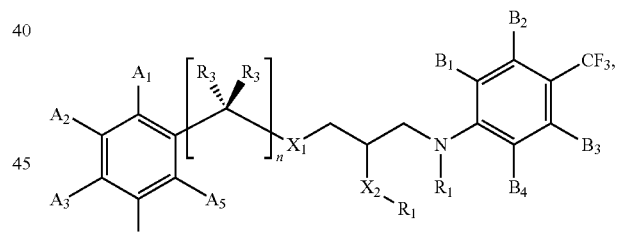
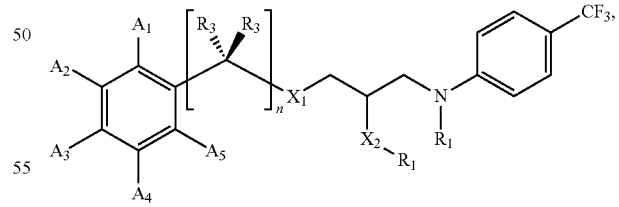
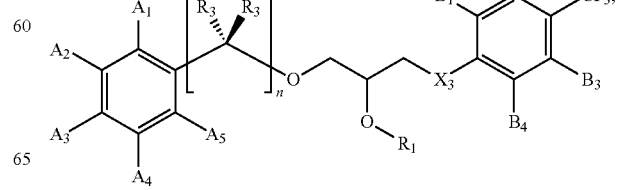

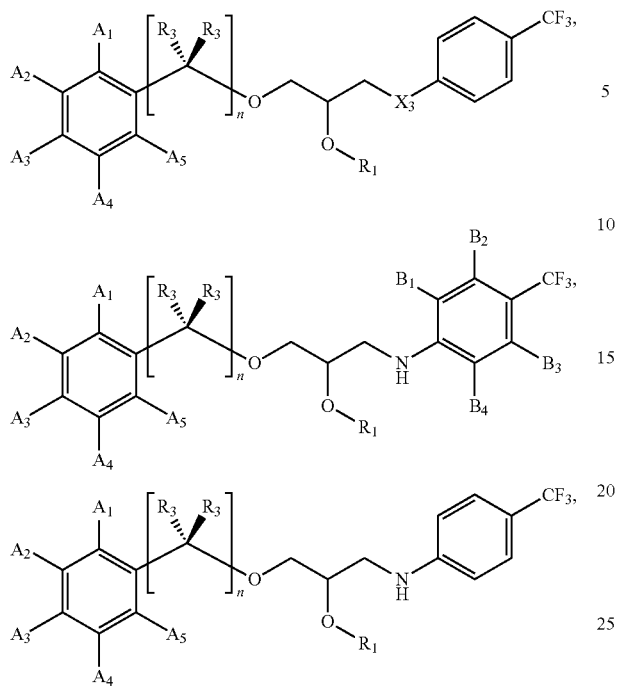
or those structures corresponding to those wherein both $R_3$ are H, the various positional isomers of the $A_1$-$A_5$ ring (as described above), the structures wherein $A_1$-$A_5$ and $B_1$-$B_4$ are all H, and the combination thereof.
Likewise, when both n and p=0, non-limiting exemplary structures include:
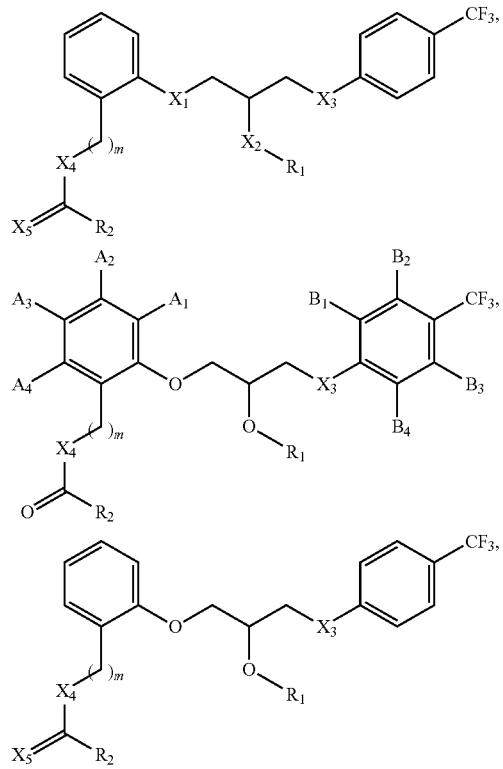
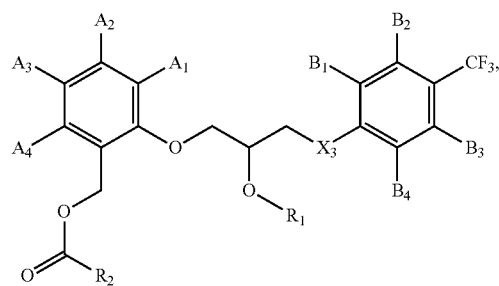
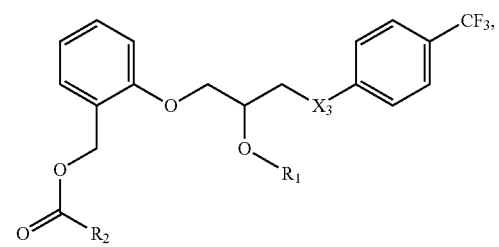
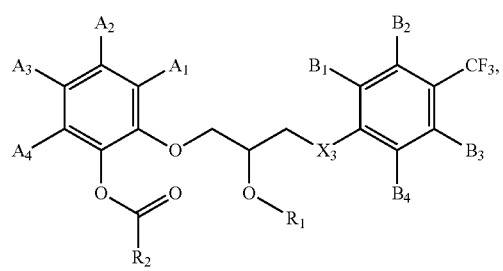

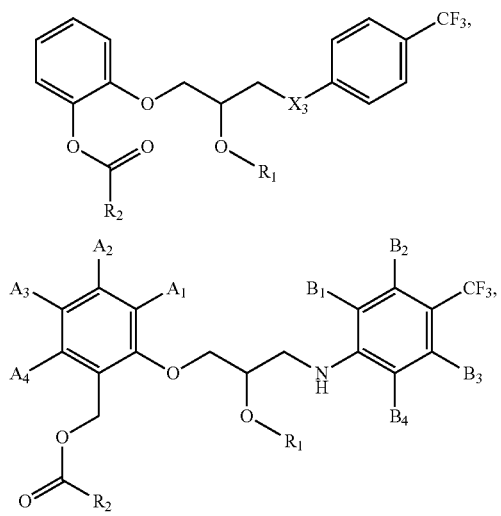
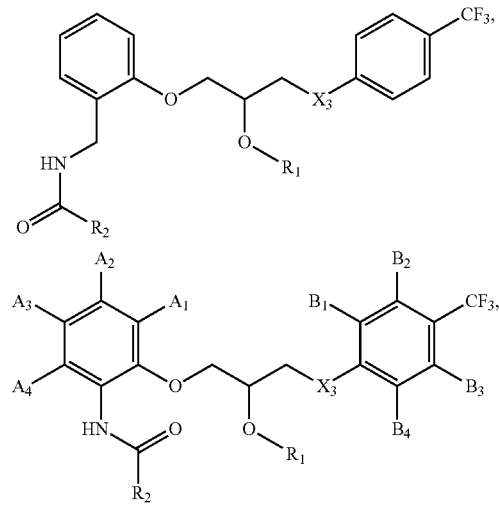
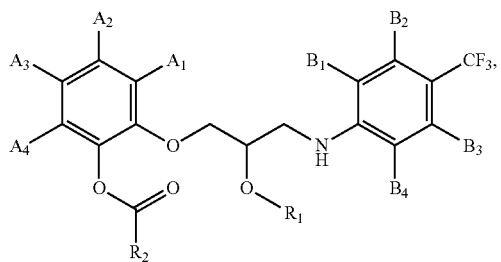
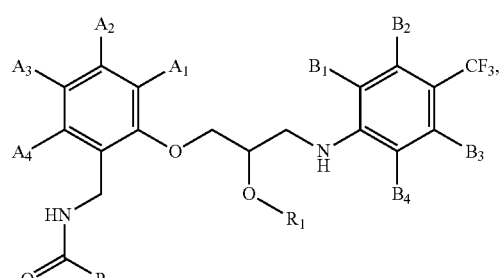
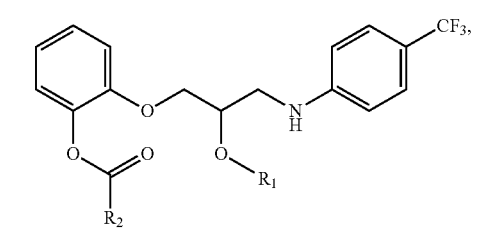
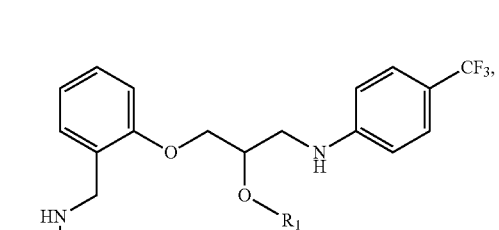
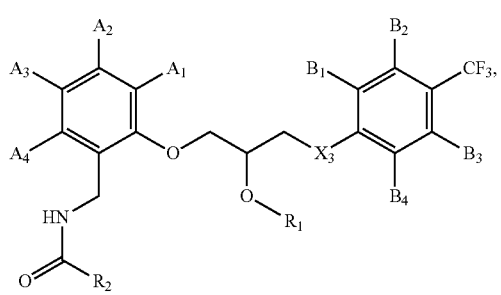
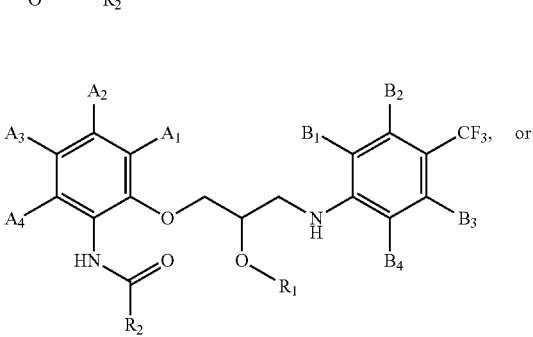

-continued

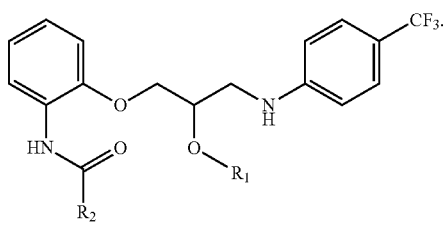

Still other embodiments include those structures specifically described in terms of:

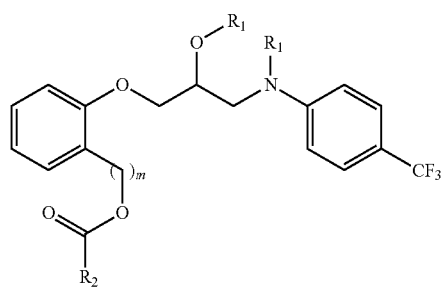

wherein $R_1$ is each independently H, linear or branched $C_{1-3}$ alkyl, or linear or branched $C_{1-3}$ acyl and $R_2$ is linear or branched $C_{1-3}$ alkyl, more specifically the compounds described by:

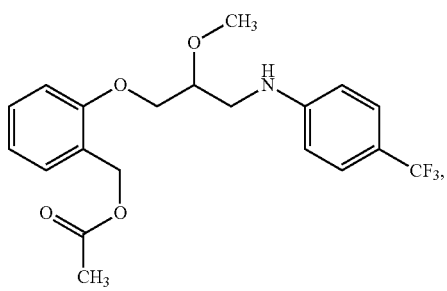

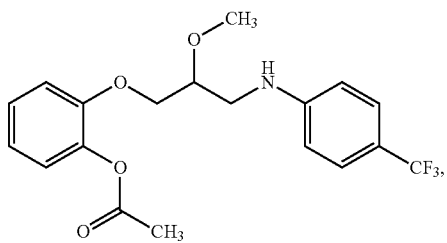

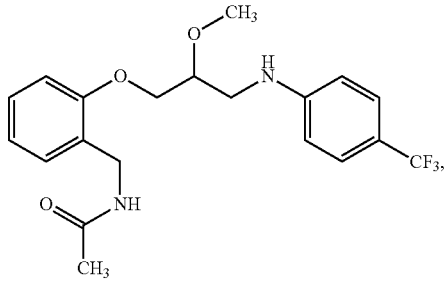

-continued

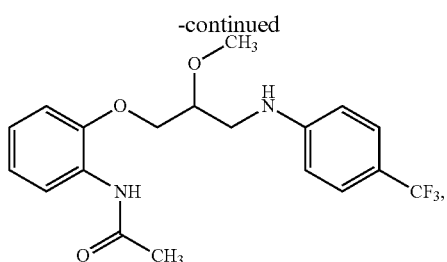

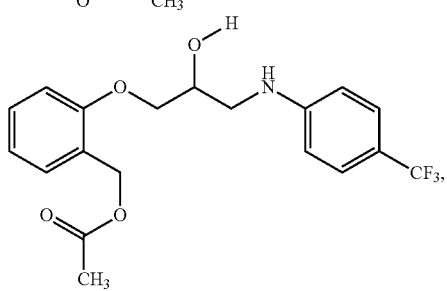

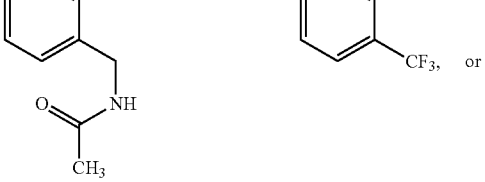

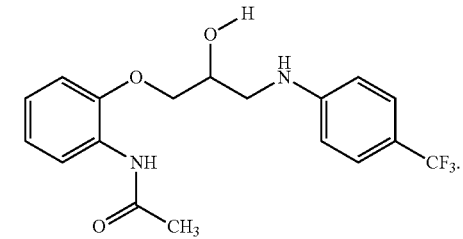, or

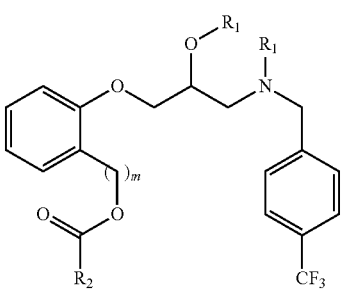

Still other embodiments include those structures specifically described in terms of:

wherein $R_1$ is each independently H, linear or branched $C_{1-3}$ alkyl, or linear or branched $C_{1-3}$ carboxyalkyl and $R_2$ is linear or branched $C_{1-3}$ alkyl, more specifically the compounds described by:

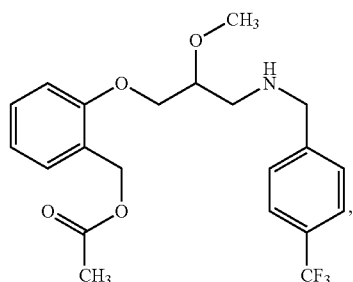

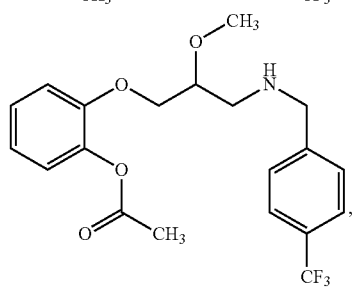

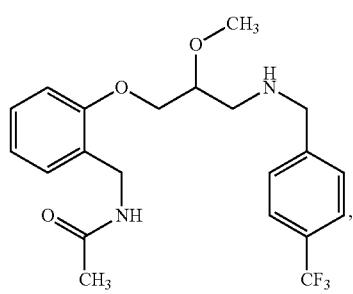

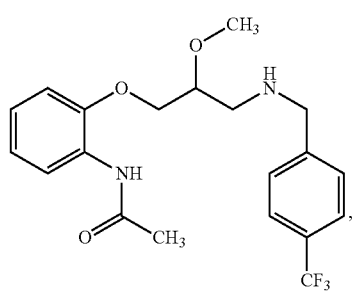

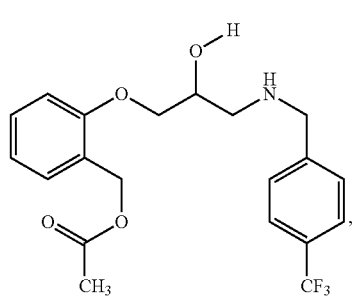

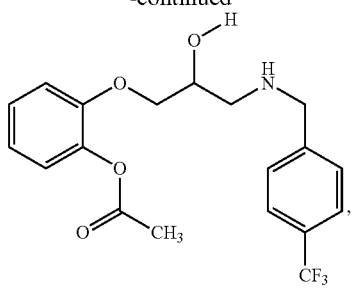

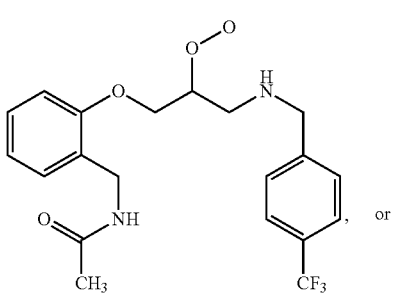

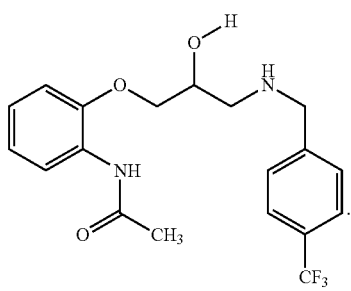

The means of preparing the compounds of the present invention are particularly described in the synthetic schemes that follow. The sequences set forth herein are illustrative only, and are not intended to limit the scope of the invention. Those skilled in the art will appreciate that modifications to the followed synthetic schemes can be performed without detracting from the spirit of the invention.

One general synthetic scheme involves the use of sequential nucleophilic attack on epichlorohydrin, and subsequent derivatization. The general methodologies for accomplishing these reactions are well known to those skilled in the art, and while not necessarily applied to the compounds described herein, the skilled artisan would not have to do undue experimentation to accomplish these transformations.

As but one example of a first step, nucleophilic displacement of the chloride by an aromatic nucleophile provides an aromatic epoxide intermediate:

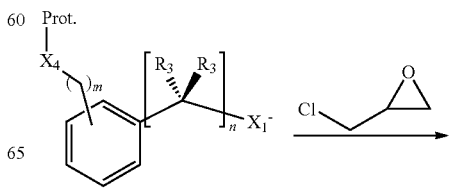

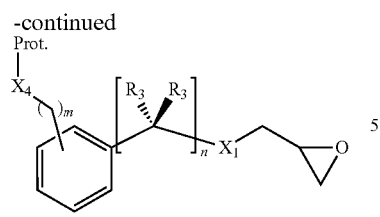

(while the phenyl group shown here is unsubstituted, except for the pendant —$(CH_2)_m$—$X_4$-Prot moiety, a skilled artisan will appreciate that the phenyl group may also contain one or more additional substituents; i.e., the remaining $A_1$-$A_5$ are omitted here simply for the sake of clarity, not as a limitation).

The optionally substituted starting materials are commercially available from a number of sources, or can be prepared by standard synthetic methods. The —$(CH_2)_m$—$X_4$-Prot moiety may be introduced to the molecule as the finally desired pendant, or may be prepared starting from the precursor protected alcohol, amine, or thiol derivative.

When n is 0, the acidity of the $X_1$ anion is stabilized by the aromaticity of the adjacent, optionally substituted phenyl ring.

When n is ultimately to be 1, a convenient starting material may include an optionally substituted benzyl alcohol, amine, or thiol, or an anion thereof, or be a precursor wherein the two $R_3$ groups together form a carbonyl. For example, when $X_1$ is to be O, the precursor benzoic acid (or benzoate) may act at the nucleophile on the epichlorohydrin. Subsequent reductions may yield the compounds wherein one $R_3$ is H, and the other is —$OR_1$, or where both are H.

In much the same way, the epoxide is susceptible to a second nucleophilic attack, with ring opening, to complete the basic molecular structure.

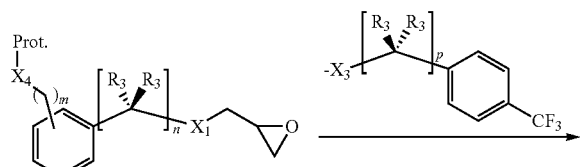
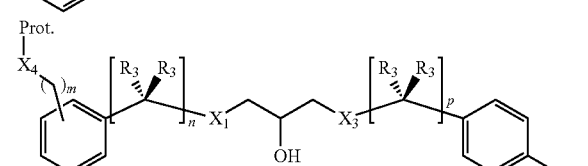
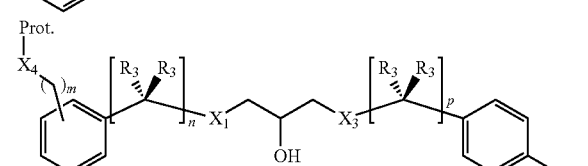

As above, $X_3$ may comprise one of various aromatic heteroatom nucleophiles, depending on the functionality required. Similarly, the central hydroxyl group can be substituted for other heteroatom, aryl, or heteroaryl moieties, using standardly available chemistries and/or can be functionalized with optionally substituted alkyl or carboxyalkyl or carboxyaryl groups as desired to form the corresponding carboxylate groups, again using standard organic transformations, optionally using amine, carboxy, or hydroxyl protecting groups as necessary, depending on the nature of the other substituents.

Such transformations are describe, for example, in J. March, Advanced Organic Chemistry: Reactions, Mechanisms, and Structures, 2d, McGraw-Hill (1977), which is incorporated by reference in its entirety for this purpose.

For example, in but one of the many variations based on this general scheme, the compound,

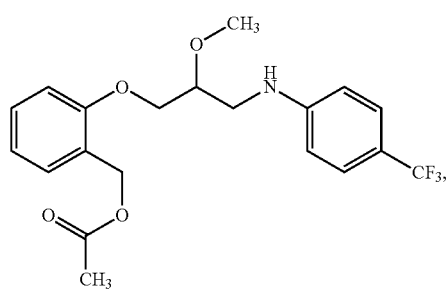 [SMILES: COC(CNc1ccc(C(F)(F)F)cc1)COc1ccccc1COC(C)=O]

was synthesized using general methodology according to:

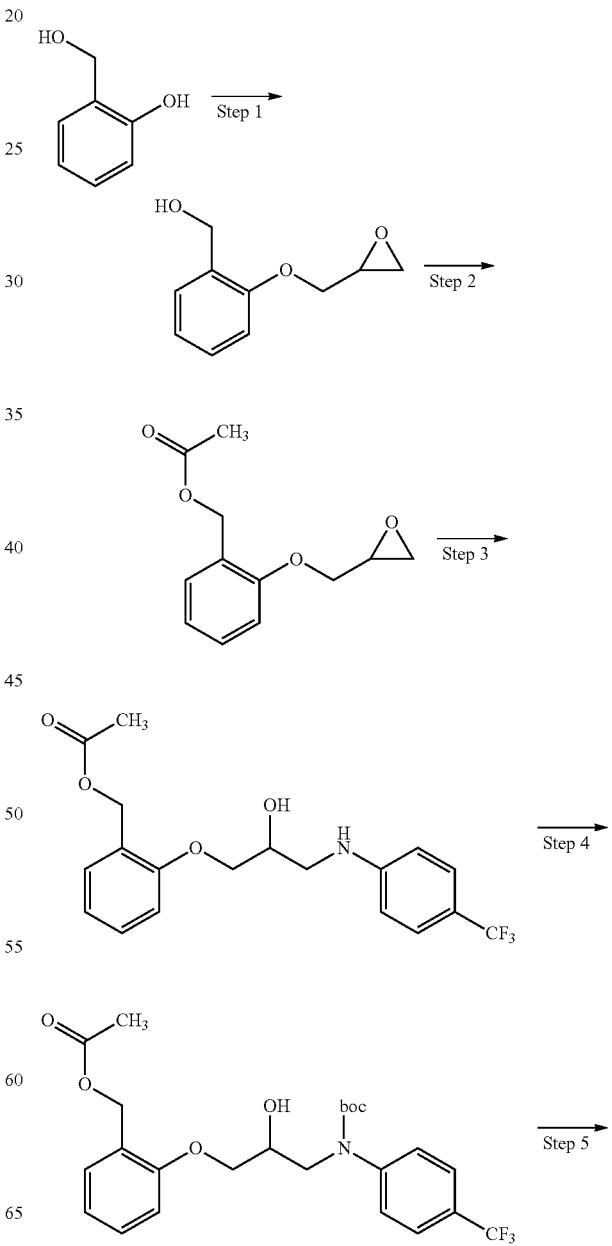

-continued

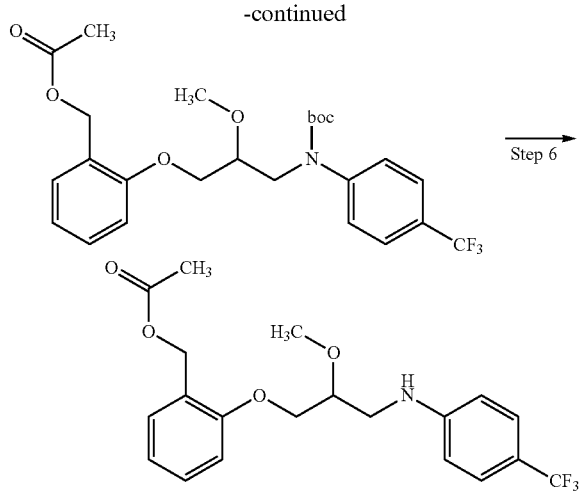

The specific details of this synthesis is described in Example 2.

Tumor Necrosis Factor Receptor

Tumor necrosis factor (TNF) receptor is one of the central mediators of inflammation. The three dimensional structure of the TNF receptor 1 (TNF-R1) complex has been determined with and without its ligand. Small molecules, described below, can bind to a discrete surface cavity and can disable ligand-induced TNF receptor functions. Although not wishing to be bound by any particular theory, it is thought that this is a consequence of the conformational perturbation of a loop on the receptor containing tryptophan-107 (W107). The conformational perturbation approach identifies surface sites that are relevant for TNF-α, receptor's biological activity in vitro and in vivo.

TNF-R1 is a transmembrane receptor glycoprotein of Mr approximately 55 kDa. The primary translation product of TNF-R1 is modified by cleavage of an amino terminal signal sequence and further by cleavage between arginine and aspartic acid residues found, respectively, approximately 11 and 12 amino acids from the signal sequence cleavage site. A soluble fragment of TNF-R1 of approximately 20 kDa can be isolated from sera and urine. The soluble fragment retains TNF-R1 binding activity. As used herein, the position of amino acids in TNF-R1 are given with reference to the sequence shown in SEQ ID NO: 1.

Although not wishing to be bound by any particular theory, the crystal structure analysis of the TNF receptor complex with and without ligands did not reveal any changes consistent with ligand induced fit. (Banner et al., Cell 73, 431 (1993)). Hence the structural role of the ligand was postulated to bring the receptor together and facilitate receptor activation. A flexible hinge (G81 and G97) identified from the crystal structure analysis was postulated to provide ligand induced conformational changes. Contrary to the result predicted if such a flexible hinge existed, however, no significant conformational changes were observed in the crystallographic complex of TNF-R1/TNF-α versus TNF-R1 alone. Thus, the crystal studies failed to suggest the presence of an allosteric site or cavity on TNF-R1.

Small molecule ligands are identified herein that can be used to induce conformational perturbations in TNF-R. While not wishing to be bound by any particular theory, in particular, the compounds described herein appear to have structures capable of being bounded by a cavity of a tumor necrosis factor receptor (TNF-R), said cavity bounded by Cys-76, Arg-77, Asp-93, Cys-96, Arg-104, Asn-110, Phe-112, and Lys-132. A pictorial description of such a compound bounded in this cavity is shown in FIG. 1.

Treatment of TNF Mediated Conditions

The term "therapeutic agent" is intended to mean a compound that, when present in a therapeutically effective amount, produces a desired therapeutic effect on a mammal. For example, an "effective amount" of a compound for inhibiting tumor necrosis factor action is an amount of a compound or composition that is sufficient to inhibit, reduce, or otherwise mitigate an undesirable effect of tumor necrosis factor action. Such inhibition may occur for example, and without limitation, via a direct interaction, and/or through a competitive interaction, or via an allosteric interaction with TNF-R1, TNF-α, or with another binding protein.

Pharmaceutical compositions containing the small molecules described below can be useful to treat individuals suffering from TNF-mediated diseases, disorders, and conditions. Examples of TNF-mediated diseases, disorders, and conditions include inflammatory diseases and autoimmune diseases such as rheumatoid arthritis (RA), multiple sclerosis (MS), Sjogren's syndrome, sarcoidosis, insulin dependent diabetes mellitus (IDDM), autoimmune thyroiditis, psoriatic arthritis, reactive arthritis, ankylosing spondylitis, scleroderma, polymyositis, dermatomyositis, psoriasis, vasculitis, Wegener's granulomatosis, Crohn's disease, pediatric Crohn's disease, ulcerative colitis, inflammatory neuropathy, Lou Gehrig's disease, Alzheimer's disease, Lupus (SLE), Grave's disease, myasthenia gravis, autoimmune hemolytic anemia, autoimmune thrombocytopenia, asthma, refractory asthma, cryoglobulinemia, primary biliary sclerosis, pernicious anemia, graft vs. host disease, septic shock, endotoxic shock and periodontal disease (e.g., gingivitis). Individuals suffering from such diseases, disorders, and conditions may be treated by administering to them a therapeutically effective amount of a pharmaceutical composition that contains a compound having formula (I) or MH_0742 or pharmaceutically acceptable salt thereof. More broadly, treatment methods of the present invention include alleviating symptoms or pathologies involving TNF, such as, by not limited to bacterial, viral or parasitic infections, chronic inflammatory diseases, autoimmune diseases, malignancies, and/or neurodegenerative diseases.

Recent evidence associates TNF with infections, immune disorders, neoplastic pathologies, autoimmune pathologies and graft-versus host pathologies. The association of TNF with cancer and infectious pathologies is often related to the host's catabolic state. Cancer patients suffer from weight loss, usually associated with anorexia. Administering a therapeutically effective amount of a pharmaceutical composition that contains a TNF antagonist compound having formula (I) or MH_0742 or pharmaceutically acceptable salt thereof, can be useful for the treatment to decrease the effects of these pathologies, including angiogenesis or cachexia.

The inhibition or antagonism of TNF has also been shown to decreases the expression of Vascular Endothelial Growth Factor (VEGF) or Vascular Permeability Factor (VPF). VEGF has been implicated in the angiogenesis in cancer, vascular diseases and rheumatoid arthritis, for example. Thus, a therapeutically effective amount of a TNF antagonist, such as a compound having formula (I) or MH_0742 or pharmaceutically acceptable salt thereof, can be administered to a mammal for the treatment to decrease angiogenesis, such as in the treatment of a VEGF-mediated disease.

Biological Activity

The activity a compound of the invention can be measured using in vivo or in vitro biological assays that measure, for example and without limitation, the ability of a compound to interfere with the biological activity of TNF-α. One example of such an assay is measuring the ability of a compound to inhibit TNF-α mediated cytolysis in L929 cells, or other suitable cells. Other examples of such assays include assaying the ability of a compound to block or inhibit an event associated with intracellular signaling following treatment with TNF-α. Examples of such signaling events include the phosphorylation of NFκB and/or p38 in L929 cells and NE91 cells. Each of these provides a useful model for in-patient effectiveness.

In one embodiment, the biological activity of a compound is measured by the ability of the compound to inhibit TNF-α mediated cytolysis of L929 cells. Compounds of the present invention include compounds that show at least 70% inhibition of TNF-α mediated cytolysis of L929 cells at a concentration as low as 100 μM or at least 60% inhibition of TNF-α mediated cytolysis of L929 cells at a concentration as low as 100 μM or at least as low as 90 μM. Compounds of the present invention include compounds that show at least 50% inhibition of TNF-α mediated cytolysis of L929 cells at a concentration as low as 100 μM, as low as 80 μM, or as low as 60 μM and/or at least 30% inhibition of TNF-α mediated cytolysis of L929 cells at a concentration as low as 100 μM, as low as 80 μM, as low as 60 μM, as low as 50 μM, or as low as 40 μM.

Salts and Derivatives

Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, hydrofluoric, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as lithium, sodium, and potassium salts; alkaline earth metal salts, such as calcium and magnesium salts; salts formed from Lewis acids, such as boron trifluoride; and salts formed with organic or inorganic ligands, such as quaternary ammonium salts (for example, tris(hydroxymethyl)aminomethane salts).

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

Prodrugs and active metabolites of compounds disclosed herein are also within the scope of the invention.

A prodrug is a pharmacologically inactive compound that is converted into a pharmacologically active agent by a metabolic transformation or any other chemical or biological process (e.g., hydrolysis). For example, in vivo, a prodrug can be acted on by naturally occurring enzyme(s) resulting in liberation of the pharmacologically active agent. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in "Design of Prodrugs," ed. H. Bundgaard, Elsevier, 1985.

An active metabolite is a compound that results from metabolism of another compound after administration of the latter to a subject. Metabolites can be identified by techniques well-known in the art.

Formulation and Administration

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds of formulae (I), (II), or (III), or a pharmaceutically acceptable salt thereof, are intimately admixed with a pharmaceutical carrier according to conventional pharmaceutical compounding techniques. The carrier may take a wide variety of forms depending on the form of preparation desired for administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules, caplets, and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

In some applications, it may be advantageous to utilize the active agent in a "vectorized" form, such as by encapsulation of the active agent in a liposome, micelle, or other encapsulant medium, or by fixation of the active agent, e.g., by covalent bonding, chelation, assembly, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g., inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams and Wilkins: Philadelphia, Pa., 2000.

The formulation of the present invention can have immediate release, sustained release, delayed-onset release or any other release profile known to one skilled in the art.

The subject receiving the pharmaceutical composition is preferably an animal, including, but not limited, to an animal such a cow, horse, sheep, pig, chicken, turkey, quail, cat, dog, mouse, rat, rabbit, and guinea pig, and is more preferably a mammal, and most preferably a human.

The amount of the active agent to be administered can typically range from between about 0.01 to about 25 mg/kg/day, preferably from between about 0.1 to about 10 mg/kg/day and most preferably from between about 0.2 to about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds are formulated in capsules or tablets, preferably containing 25 to 200 mg of the compounds of the invention, and are preferably administered to a patient at a total daily dose of about 0.5 mg to about 2 g, preferably about 7.5 mg to about 750 mg, more preferably about 15 mg to 750 mg, and most preferably from about 50 to about 200 mg.

A pharmaceutical composition for parenteral administration contains from about 0.01% to about 100% by weight of the active agents of the present invention, based upon 100% weight of total pharmaceutical composition.

EXAMPLES

The following examples illustrate the invention, but are not limiting.

Example 1

Materials

L929 cultured murine fibroblast cells were obtained from American Type Culture collection (Manassas, Va.). TNF-α was obtained from Roche Applied Science (T6674). Actinomycin D (ACTD) and Crystal Violet were obtained from Sigma-Aldrich. Testing compounds were dissolved in DMSO at 25 mM. Compounds F001 and FT002/F002, appearing in FIG. 3 and FIG. 2/FIG. 4, were described previously in application Ser. No. 11/815,134 as FIGS. 1-6 and 1-9, respectively, and are reproduced here for reference. Compound 71023, appearing in FIG. 1, was ([(aminocarbothioyl)amino]{[4-({[[(aminocarbothioyl)amino](ammonio)methyl]amino}methyl)-2,5-dimethylbenzyl]amino}methylidene)ammonium dichloride, available from Maybridge Chemicals, UK. Compound MH_072 (also described herein as the compound of formula (II)) was also obtained from Maybridge Chemicals, UK. Compound MH_0724 was synthesized by Sapient Discovery, San Diego, Calif., as described in Example 2.

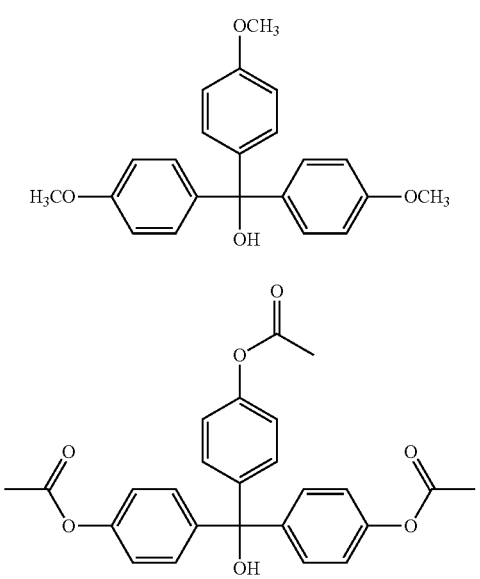

Example 2

Synthesis of Compound MH_0724

The scheme used to prepare this compound is provided as above:

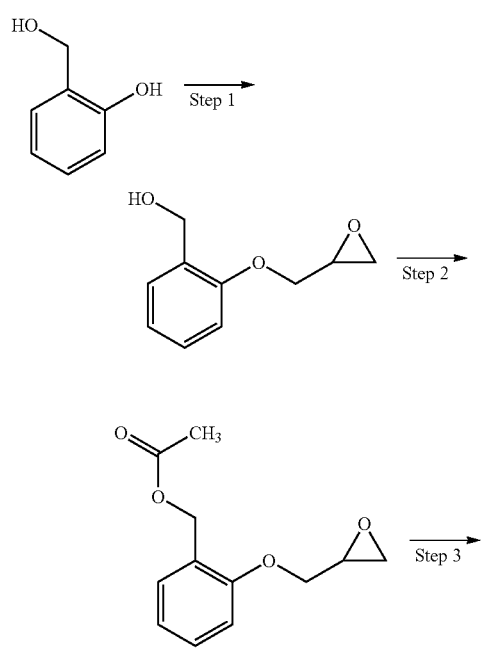

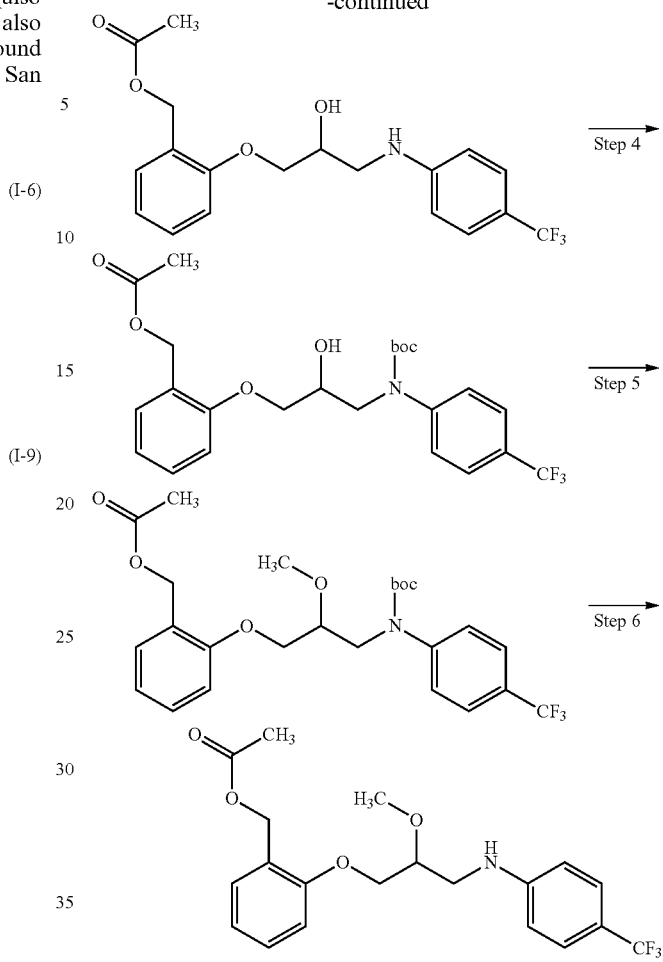

All the key raw materials were sourced from Sigma-Aldrich, and solvents were dried before using.

Step 1: Synthesis of (2-Oxiranyl-methoxy-phenyl) methanol (Compound 2)

2-Hydroxy benzyl alcohol (5 g; 0.04 mol; 1 eq.) was dissolved in dry acetone (100 mL) under nitrogen, to which was added dry $K_2CO_3$ (11 g; 0.08 mol; 2 eq.) and KI (6.6 g; 0.04 mol; 1 eq.) followed by dropwise addition of epichlorohydrin (5.5 g; 0.06 mol; 1.5 eq.). The mixture was stirred at 65° C. for 12 hours. The reaction mixture was poured into ice water; and the aqueous layer was extracted with dichloromethane (2×50 mL). The combined organic layers were washed with brine and concentrated. Crude compound was purified by column chromatography (silica, pet ether:EtOAc, 90:10, 80:20) to get 3.5 g of the desired product. $^1$H-nmr (CDCl$_3$) δ: 7.31 (2H, m); 7.00 (1H, m); 6.90 (1H, m); 4.73 (2H, m); 4.35 (1H, m); 4.06 (1H, m); 3.39 (1H, m); 2.94 (1H, m); 2.84 (1H, m); 2.06 (1H, br).

Step 2: Synthesis of Acetic acid 2-oxiranylmethoxy-benzyl ester (Compound 3)

The preceding product, Compound 2 [(2-oxiranyl-methoxy-phenyl) methanol] (3.2 g; 0.017 mol; 1 eq.) and triethylamine (3.5 g; 0.034 mol; 2 eq.) were dissolved in dry dichloromethane (32 mL) at room temperature. The reaction mixture was cooled to 0° C. and neat acetyl chloride (1.6 g; 0.021 mol; 1.2 eq.) was added drop wise. The mixture was stirred at 0-10° C. for 3 hours. The reaction mixture was poured into ice water and the aqueous layer was extracted with dichloromethane (2×100 mL). The combined organic layers were washed with brine and concentrated. Crude compound was purified by column chromatography (silica, pet ether:EtOAc, 95:5, 90:10) to afford 1.8 g of the desired product. $^1$H-nmr (CDCl$_3$) δ: 7.32 (2H, m); 7.00 (1H, m); 6.93 (1H, m); 5.21 (2H, s); 4.28 (1H, m); 4.02 (1H, m); 2.92 (1H, m); 2.92 (1H, m); 2.79 (1H, m); 2.12 (3H, s).

Step 3: Synthesis of Acetic acid 2-[2-hydroxy-3-(4-trifluoromethyl-phenylamino)-propoxy]-benzyl ester (Compound 4)

The preceding product, Compound 3 [acetic acid 2-oxiranylmethoxy-benzyl ester] (1.8 g, 0.008 mol, 1 eq.) was added to 4-trifluoromethyl aniline (1.43 g, 0.009 mol, 1.1 eq.). LiBr (1.4 g, 0.016 mol, 2 eq.) was added portion-wise to the stirring mass, and the mixture was stirred at room temperature for 3 hours. The reaction mixture was poured into ice water; aqueous layer was extracted with EtOAc (2×50 mL). The combined organic layers were washed with brine and concentrated. Crude compound was purified by column chromatography (silica, pet ether:EtOAc, 70:30, 50:50) to afford 1 g of the desired product. $^1$H-nmr (CDCl$_3$) δ: 7.23 (4H, complex multiplet); 7.03 (1H, m); 6.85 (1H, m); 6.79 (2H, m); 5.26 (2H, m); 4.30 (1H, m); 4.17 (1H, m); 4.05 (1H, m); 3.44 (1H, m); 3.35 (1H, m); 2.09 (3H, s).

Step 4: Synthesis of Acetic acid 2-{3-[tert-butoxycarbonyl-(4-trifluoromethyl-phenyl)-amino]-2-hydroxy-propoxy}-benzyl ester (Compound 5)

The preceding product, Compound 4 [acetic acid 2-[2-hydroxy-3-(4-trifluoromethyl-phenylamino)-propoxy]-benzyl ester] (1. g, 0.003 mol, 1 eq.) was dissolved in dry dichloromethane (15 mL) at 0° C. under nitrogen. To this was added triethylamine (0.46 g, 0.0045 mol, 1.5 eq.) followed by dropwise addition of BOC anhydride (0.8 g, 0.0036 mol, 1.2 eq.) and the mixture was room temperature for 48 hours. Ice water was added to the reaction mixture was added ice water, and the aqueous layer was extracted with dichloromethane (2×50 mL). The combined organic layers were washed with brine and concentrated. Crude compound was purified by column chromatography (silica, pet ether:EtOAc, 85:15) to afford 800 mg of the desired product. $^1$H-nmr (CDCl$_3$) δ: 7.28-7.43 (4H, complex multiplet); 7.04 (1H, m); 6.90 (1H, m); 6.70 (2H, m); 5.20 (3H, m); 4.21 (2H, m); 3.66 (2H, m); 2.11 (3H, s); 1.51 (9H, s). M+1=484.0 (calc'd 482.5).

Step 5: Synthesis of Acetic acid 2-{3-[tert-butoxycarbonyl-(4-trifluoromethyl-phenyl)-amino]-2-methoxy-propoxy}-benzyl ester (Compound 6)

The preceding product Compound 5 [acetic acid 2-{3-[tert-butoxycarbonyl-(4-trifluoromethyl-phenyl)-amino]-2-hydroxy-propoxy}-benzyl ester] (0.3 g, 0.69 mmol, 1 eq.) was dissolved in methyl iodide (3 mL) at room temperature, to which was added Ag$_2$O (0.18 g, 0.8 mmol, 1.2 eq) and the mixture was allowed to stir for 12 hours. The reaction mixture was concentrated and purified by flash column chromatography (silica, pet ether:EtOAc, 90:10) to afford 100 mg of the desired product. The formation of this product was confirmed only by LCMS, but was otherwise not analytically characterized before taking to the next and final step.

Step 6: Synthesis of Acetic acid 2-[2-methoxy-3-(4-trifluoromethyl-phenylamino)-propoxy]-benzyl ester (Compound MH_0724)

The preceding product, Compound 6 [acetic acid 2-{3-[tert-butoxycarbonyl-(4-trifluoromethyl-phenyl)-amino]-2-methoxy-propoxy}-benzyl ester] (0.1 g, 0.2 mmol, 1 eq.) was dissolved in dry dichloromethane (10 mL) at room temperature, then cooled to 0° C. after which trifluoroacetic acid (5 mL) was added dropwise, the mixture warmed to room temperature and stirred for 2 hours. The reaction mixture was concentrated and purified by preparative HPLC (see next Table) to afford 22 mg of the final compound. $^1$H-nmr (CDCl$_3$) δ: 7.47 (2H, m); 7.35 (2H, m); 7.03 (1H, m); 6.87 (1H, m); 6.82 (2H, m); 5.27 (2H, dd); 4.30 (1H, m); 4.06 (2H, dm); 3.64 (2H, m); 3.10 (3H, s); 2.09 (3H, s). M+1=397.9 (calc'd 397.4).

TABLE

| Conditions for preparative chromatography | |
|---|---|
| Column | Symmetry C18, 19 × 300 mm |
| Mobile phase | A = 0.1% TFA in water |
| | B = Methanol |
| Flow rate | 15.5 mL/min |
| Wavelength | 254 and 220 nm |
| Runtime | 22 min |
| Retention time | 13.142 min |

| Gradient Programming | | |
|---|---|---|
| Time (min) | Mobile Phase A (wt %) | Mobile Phase-B (wt %) |
| 0 | 40 | 60 |
| 12 | 2 | 98 |
| 16 | 2 | 98 |
| 16.1 | 40 | 60 |
| 20 | 40 | 60 |

Example 3

Cell Cultures hTNF-α was obtained from Sigma (Cat # T6674). Antibodies for IκB, phospho-IκB, p38, and phospho-p38 were purchased from Cell Signaling.

Stock L929 cells were grown on tissue culture plastic in complete Dulbecco's Modified Eagle Medium (DMEM) supplemented with 5 weight percent FBS [Fetal Bovine Serum], NEAA [non-essential amino acids], and glutamine. In a first set of experiments, L929 cells were plated using the same medium on 96-well tissue culture plates at high density (i.e., 30,000 cells/well) before use. In a second set of experiments, the testing compounds were pre-incubated with cells for 1 hour. hTNF-α (10 ng/ml) was added to cells for 30 minutes. Cell lysates were then collected for routine Western Blot.

Human TNFR1 ectodomain was expressed in bacteria as described Murali, et al., 2005 PNAS 102:10970-75, which is incorporated by reference herein in its entirety. The His-tagged recombinant protein was purified from bacterial cell lysate using Ni-NTA column About 4 mg proteins were obtained from 6 liters of culture. The purified TNFR1 ectodomain was verified for binding activity to hTNF-α in ELISA assay.

Example 4

Cell Treatments

Approximately 20 hours after plating the L929 cells on 96-well plates, they were re-fed onto fresh medium containing the test compounds (from 0 to 100 μM, final concentration).

For the TNF-α challenges, approximately 30 minutes later, medium containing 4 unit/mL rh-TNF-α and actinomycin D (10 μg/mL) was added. The final concentrations of rh-TNF-α in the assays were 312.5 μg/mL, which is the ED50 concentrations confirmed to induce 50% cell death. The final concentrations of actinomycin D in the assays were 2.5 μg/mL. The plates were incubated for an additional 16-20 hours at 37° C., 5 vol % $CO_2$ in air.

For Crystal Violet staining, the culture medium was discarded and replaced with 0.2% by weight (in 2% by volume ethanol in water), 100 μL/well. After 15 minutes incubation at room temperature, the plates were washed 6 times with deionized water and dried at 37° C. for 40 minutes. Sodium dodecylsylfate (SDS), (1 wt % in water; 100 μL) was added to each well and mixed gently for 1 hour at room temperature. The plates were read at A570 nm Isothermal Titration calorimetry (ITC). The binding thermodynamics of MH724 to TNFR1 was measured by ITC using a high precision VP-ITC titration calorimetric system (Microcal LLC, Northampton, Mass.). The calorimetric cell containing purified TNFR1 ectodomain at a concentration of 0.1 mM in 50 mM sodium phosphate buffer (pH 8.0) containing 300 mM NaCl and 5% DMSO was titrated with MH724 dissolved in the same buffer. The concentration of inhibitor was 2 mM. Injection volumes were 8 μl. All solutions were properly degassed to avoid any formation of bubbles in the calorimeter during stirring. The heat evolved upon each injection of inhibitor was obtained from the integral of the calorimetric signal. The heat associated with the binding of the inhibitor to TNFR1 was obtained by subtracting the heat of dilution from the heat of reaction. The measurements were made at 25° C. Data were analyzed and fitted by using the data analysis software supplied by Microcal (ORIGIN 5.0).

Example 5

Results of First Set of Experiments

Figure 2:
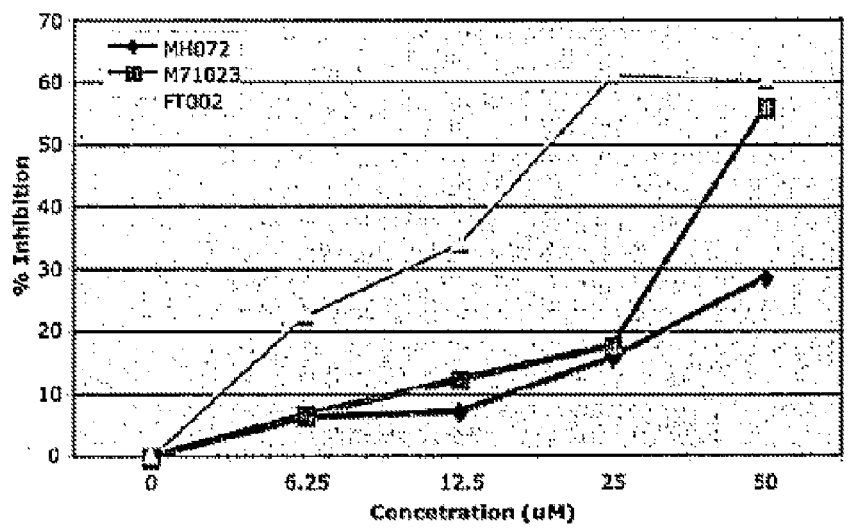
FIG. 2 illustrates the inhibitory effect of MH072 on TNF-α mediated cytolysis as a function of concentration.
Figure 3:
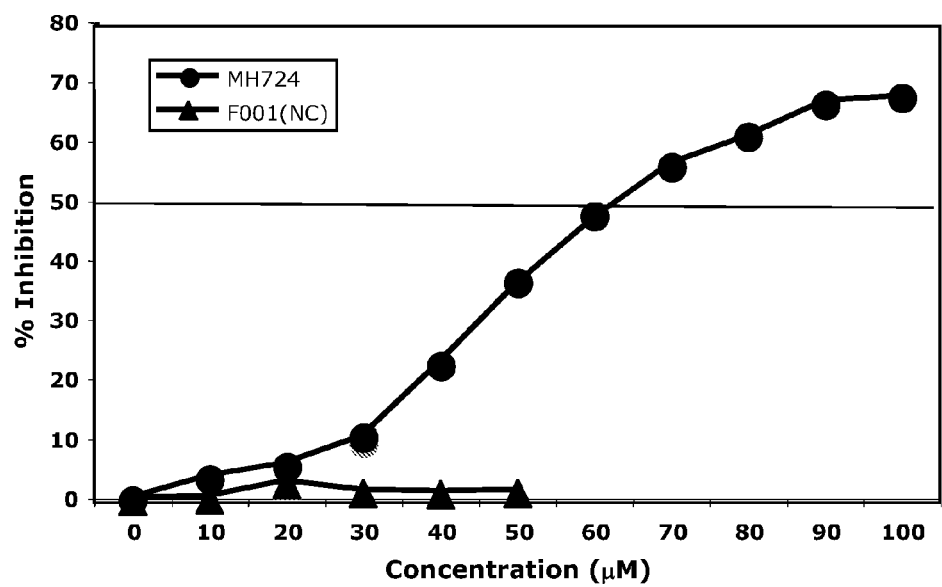
FIG. 3 illustrates the inhibitory effect of MH724 on TNF-α mediated cytolysis as a function of concentration.

The results of the testing in Example 4 are shown in FIG. 2 and FIG. 3.

MH_072 (FIG. 2) demonstrated a dose-dependent inhibition of TNF-α-induced cytolysis in L929 cells from 0 to 50 μM; MH072 is soluble under these conditions only up to 50 μM. The compound MH072 showed a maximum of about 30% inhibition in the same assay, this level apparently limited by the limits of solubility of the MN072 under these conditions.

MH_0724 (FIG. 3) demonstrated a dose-dependent inhibition of TNF-α-induced cytolysis in L929 cells from 0 to 100 μM. Even at 50 μM, MH724 exhibited improved inhibitory activity relative to the MH072 (ca. 40% vs. 30%). The maximal inhibition by 100 μM of MH724 was significantly higher at ca. 70% and comparable to that exhibited by 500 ng/mL of anti-TNFα antibody (data not shown). The control compound F001 showed minimal activity under the same conditions.

The data indicated that MH_0724 has improved activity over MH_072 (about 40% inhibition at 50 μM).

Example 6

Results of Second Set of Experiments

Figure 4:
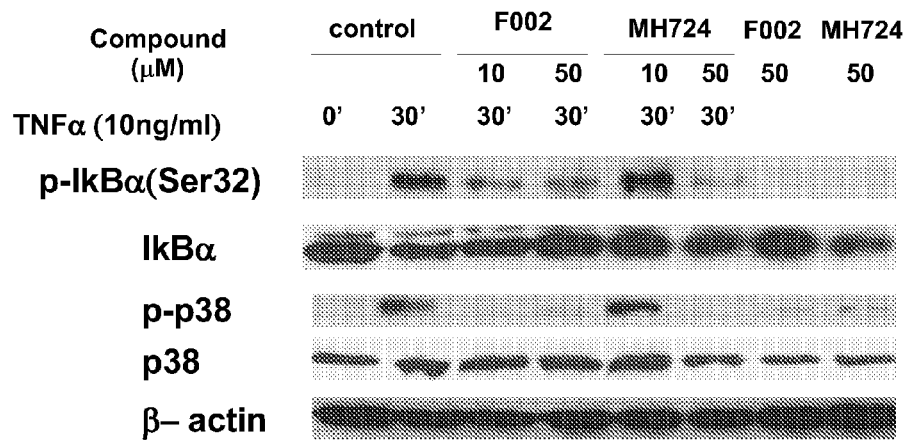
FIG. 4 illustrates effect of MH724 on TNFα signaling pathways.

Inhibition of TNFα signaling pathways: Upon binding to TNFRs, TNFα induces inflammation through the activation of NFκB and p38 signaling pathways. We determined IκB and p38 effects. IκB is the inhibitor for NFκB. TNFα leads to the phosphorylation and disassociation of IκB from NFκB, a signaling event required for NFκB to become activated and translocate into the nucleus to mediate gene transcription. As shown in FIG. 4, MH724 clearly inhibits the TNFα-induced phosphorylation of IκB (p-IκBα(Ser32) panel) and p38 (p-p38 panel) at the concentration of 50 μM. The previously described CIAM Compound F002 appears to have slightly more activity at 10 μM, but MH724 demonstrates better activity at 50 μM.

Figure 5:
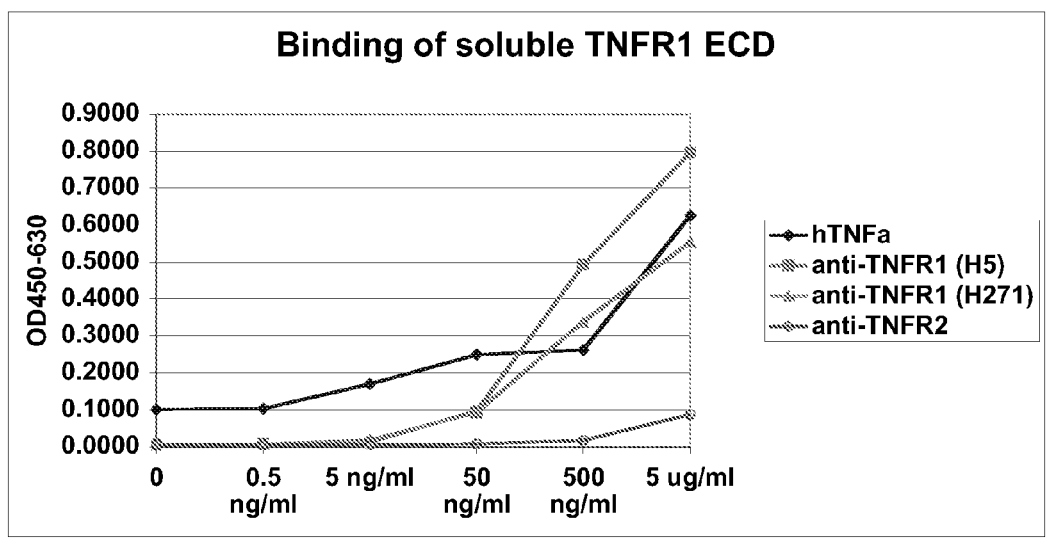
FIG. 5 illustrates the binding of recombinant TNFR1 ectodomain to TNFα and anti-TNFR1 antibodies.

Binding of MH724 to TNFR1 by ITC: Recombinantly expressed TNFR1 ectodomain (TNFR1 ECD) was first evaluated in ELISA assays for binding to TNF-α and anti-TNFR antibodies. As shown in FIG. 5, TNFR1 ECD was recognized by two anti-TNFR1 antibodies but barely by anti-TNFR2 antibody. Most importantly, TNFR1 ECD can bind to human TNF-α, indicating that this recombinant protein is structurally folded correctly and can be used for the ITC binding study.

Figure 6:
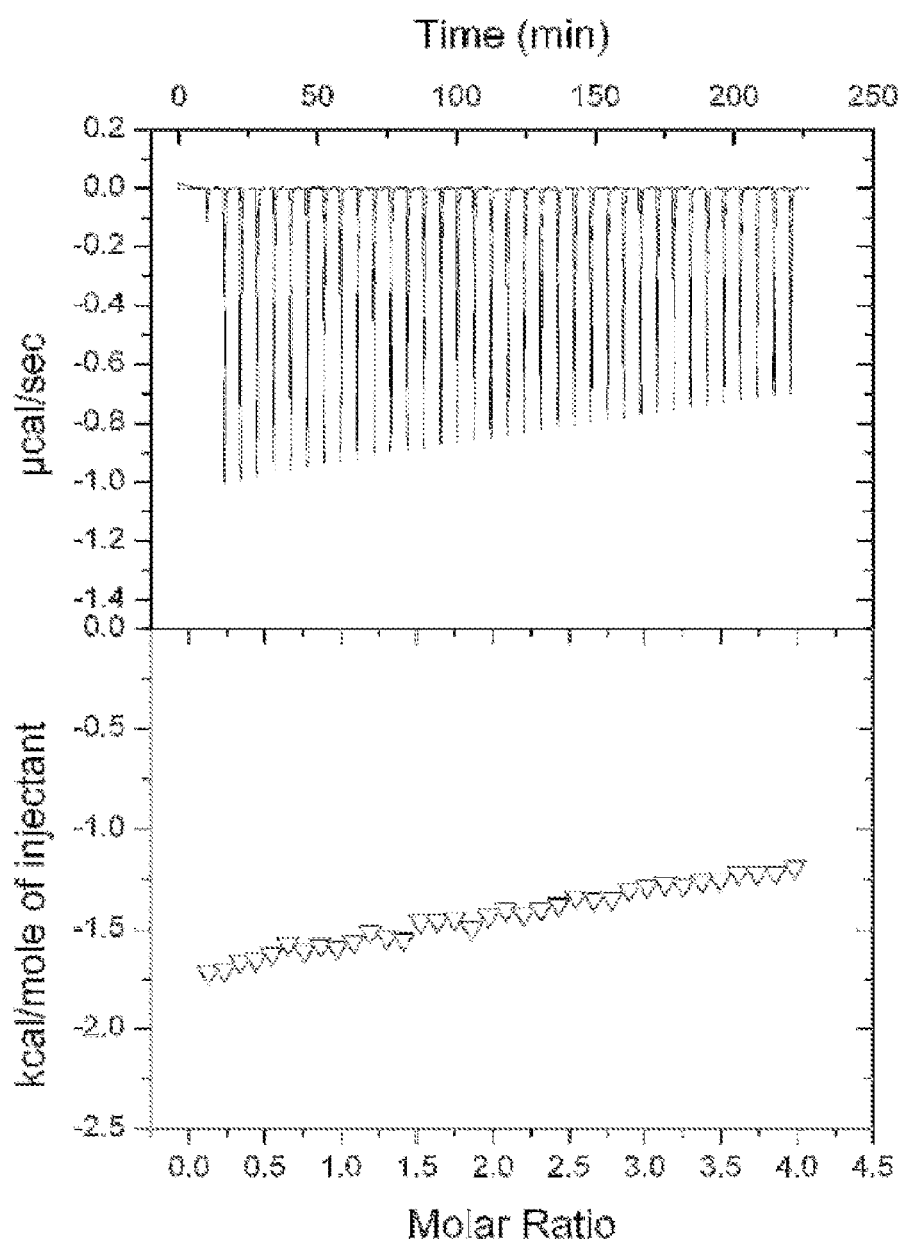
FIG. 6 illustrates the binding of MH724 to TNFR1 ECD.

The ITC study detects the binding of MH724 to TNFR1 (FIG. 6). According to the analysis, the affinity between MH724 and TNFR1 ECD is estimated to be 32 μM. This level of binding affinity is in consistent with the activity we observed for MH724 in TNFα-induced cytolysis and signaling studies in L929.

Example 7

Inhibition of TNFα Mediated NFκB Activity by TNF Inhibitors Using a Luciferase Reporter System Nuclear Factor kappa B (NFκB) is a member of the rel family of transcription factors and plays a key role in the regulation of inflammatory response downstream of TNF signaling. In the inactive state, NFκB forms a cytoplasmic complex with Inhibitory kappa B Protein (IκB). Upon stimulation, several types of kinases belonging to the mitogen-activated protein kinase (MAPK) family phosphorylate IκB, which subsequently dissociates from NFκB and undergoes degradation. The NFκB protein then translocates to the nucleus where it binds to its specific DNA motifs and initiates transcription of genes.

To study TNFα mediated-NFκB activity, a luciferase reporter system was established. The stable cell line A549Luc was derived from human A549 cells with chromosomal integration of a luciferase reporter construct regulated by 6 copies of the NFκB response element. This clonal cell line was obtained by co-transfection of pNFκB-TA-luc and pFLAG-TNFR1-neo followed by G418 selection at 800 μg/ml. A549Luc cells were pre-treated with inhibitors at indicated concentrations for 1 hr before incubation with 20 ng/ml TNFα for 4 hours. Increased luciferase activity was recorded after TNFα treatment. Luciferase activity was determined using the Luciferase Assay System from Promega.

Figure 7:
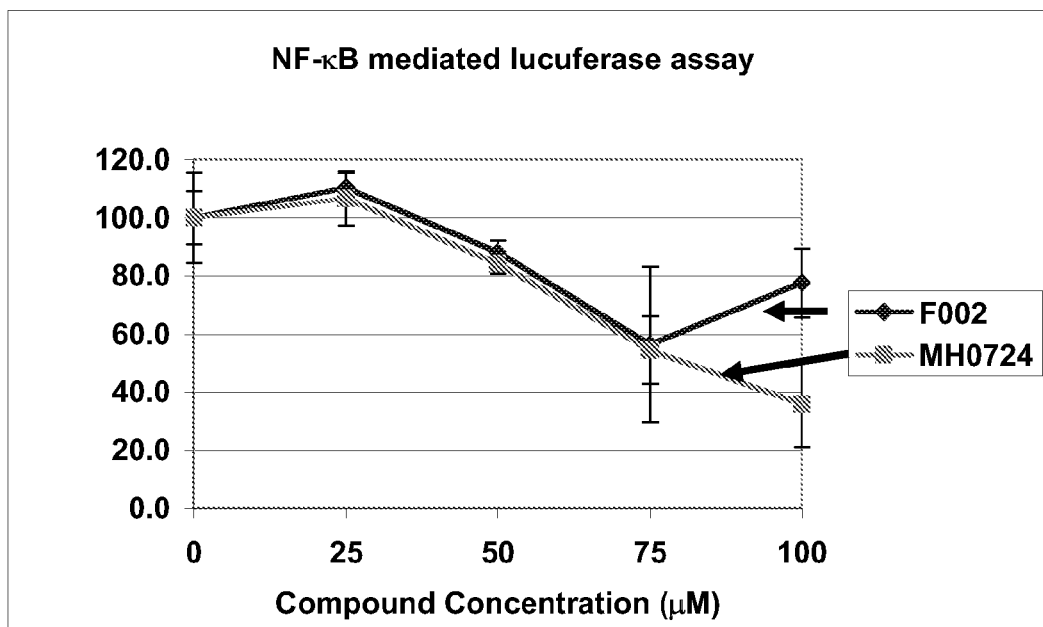
FIG. 7 charts the inhibition of TNFα mediated luciferase activity against several compounds.

As shown in FIG. 7, both F002 and MH0724 were able to inhibit the TNFα mediated luciferase activity in a dose-dependent manner. In this assay, the luciferase activity of A549Luc cells before and after TNFα treatment (20 ng/ml) was equivalent to 0% and 100%, respectively. Both F002 and MH0724 had comparable activity to reduce luciferase activity at concentrations up to 75 μM. At 100 μM, MH0724 had better activity and the luciferasae activity was reduced to less than 40% of the control.

It is understood that while the data presented for MH724 were derived from that compound, these data are believed to represent the approximate or minimal properties associated with the various compounds claimed herein. Accordingly, additional embodiments of the invention include those combinations of any of the compounds of the present invention and the specific values cited, including those for binding energies or percent inhibition, both where the specific values constitute approximate or minimal values attributable to those compounds.

The above specification, examples and data provide a description of the manufacture and use of the composition of the invention. Since many embodiments of the invention can be made without departing from the spirit and scope of the invention, the invention also resides in the claims hereinafter appended.

All references, including publications, patents, and patent applications, cited herein are incorporated herein by reference.

What is claimed:

1. A compound having the structure of formula I:

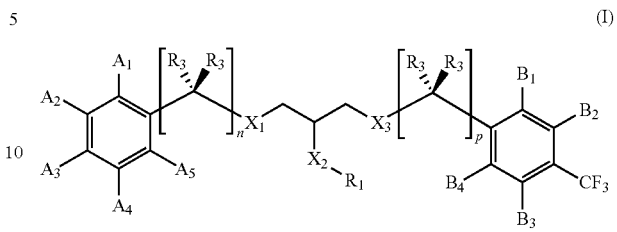

wherein, $A_1$-$A_5$ and $B_1$-$B_4$ are independently H, halo, hydroxyl, nitro, cyano, optionally substituted alkyl, optionally substituted alkoxy, optionally substituted acyl, —$(CH_2)_m$—$S(O)_qR_2$, —$N(R_1)_2$, —$(CH_2)_m$—$X_4$—$C(X_5)$—$R_2$, —$(CH_2)_m$—$C(X_5)$—$X_4$—$R_2$, —O—$(CH_2)_m$—$X_4$—$C(X_5)$—$R_2$, —O—$(CH_2)_m$—$C(X_5)$—$X_4$—$R_2$, —$SO_3H$, or —$S(O)_q$—$R_1$, or one or more pairs of $A_1$-$A_2$ or $A_2$-$A_3$ or $A_3$-$A_4$, or $A_4$-$A_5$ or $B_1$-$B_2$ or $B_3$-$B_4$, together with the respective carbons to which they are attached, form a $C_{4-8}$ alkyl, heteroalkyl, aryl, or heteroaryl ring, provided that at least one of $A_1$-$A_5$ moieties comprises—$(CH_2)_m$—$X_4$—$C(X_5)$—$R_2$;

$X_1$, $X_2$, and $X_5$ are O;

SEQUENCE LISTING

<160> NUMBER OF SEQ ID NOS: 1

<210> SEQ ID NO 1
<211> LENGTH: 172
<212> TYPE: PRT
<213> ORGANISM: Homo sapiens

<400> SEQUENCE: 1

```
Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20                  25                  30

Cys His Lys Gly Thr Tyr Leu Tyr Asn Asp Cys Pro Gly Pro Gly Gln
        35                  40                  45

Asp Thr Asp Cys Arg Glu Cys Glu Ser Gly Ser Phe Thr Ala Ser Glu
    50                  55                  60

Asn His Leu Arg His Cys Leu Ser Cys Ser Lys Cys Arg Lys Glu Met
65                  70                  75                  80

Gly Gln Val Glu Ile Ser Ser Cys Thr Val Asp Arg Asp Thr Val Cys
                85                  90                  95

Gly Cys Arg Lys Asn Gln Tyr Arg His Tyr Trp Ser Glu Asn Leu Phe
            100                 105                 110

Gln Cys Phe Asn Cys Ser Leu Cys Leu Asn Gly Thr Val His Leu Ser
        115                 120                 125

Cys Gln Glu Lys Gln Asn Thr Val Cys Thr Cys His Ala Gly Phe Phe
    130                 135                 140

Leu Arg Glu Asn Glu Cys Val Ser Cys Ser Asn Cys Lys Lys Ser Leu
145                 150                 155                 160

Glu Cys Thr Lys Leu Cys Leu Pro Gln Ile Glu Asn
                165                 170
```

$X_4$ is independently O or NH;

$X_3$ is $NR_1$;

m, n, and p and are each independently 0 or 1; q is 0, 1, or 2;

$R_1$ is independently in each case H, or optionally substituted aryl, heteroaryl, alkyl, or acyl;

$R_2$ is optionally substituted alkyl, aryl, or heteroaryl;

$R_3$ is independently in each case H, $R_1$, —$OR_1$, or when taken together with another $R_3$ attached to the same carbon is =O;

and provided that the compound does not have the structure of formula II:

(II)

2. The compound of claim 1 wherein said compound is capable of binding in a cavity of a tumor necrosis factor receptor (TNF-R), said cavity bounded by Cys-76, Arg-77, Asp-93, Cys-96, Arg-104, Asn-110, Phe-112, and Lys-132 of SEQ ID No. 0001.

3. The compound of claim 1 wherein $A_5$ is —$(CH_2)_m$—$X_4$—$C(X_5)$—$R_2$.

4. The compound of claim 1 wherein $X_3$ is NH.

5. The compound of claim 3 wherein $A_1$, $A_2$, $A_3$, and $A_4$ are H.

6. The compound of claim 1 wherein $A_4$ is —$(CH_2)_m$—$X_4$—$C(X_5)$—$R_2$ and wherein $A_1$, $A_2$, $A_3$, and $A_5$ are H.

7. The compound of claim 1 wherein $A_3$ is —$(CH_2)_m$—$X_4$—$C(X_5)$—$R_2$ and wherein $A_1$, $A_2$, $A_4$, and $A_5$ are H.

8. The compound of claim 4 wherein m=0 or 1, $X_5$ is O, and $R_2$ is $C_{1-3}$ linear alkyl.

9. The compound of claim 8 wherein —$(CH_2)_m$—$X_4$—C(O)—$R_2$ is —$(CH_2)$—$X_4$—$C(O)CH_3$.

10. The compound of claim 8 wherein —$(CH_2)_m$—$X_4$—C(O)—$R_2$ is —$X_4$—$C(O)CH_3$.

11. The compound of claim 1 wherein n=0.

12. The compound of claim 3 wherein n=0.

13. The compound of claim 1 wherein p=0.

14. The compound of claim 3 wherein p=0.

15. The compound of claim 1 or 3, wherein n=p=0.

16. The compound of claim 1 wherein $R_1$ is linear or branched $C_{1-3}$ alkyl or branched $C_{1-3}$ carboxyalkyl and $R_2$ is linear or branched $C_{1-3}$ alkyl or linear.

17. The compound of claim 16 wherein $R_1$ and $R_2$ are each independently fluorinated or perfluorinated.

18. The compound of claim 1 having the structure:

or wherein $R_1$ is each independently H, linear or branched $C_{1-3}$ alkyl, or linear or branched $C_{1-3}$ carboxyalkyl and $R_2$ is linear or branched $C_{1-3}$ alkyl.

19. The compound of claim 18 having the structure:

or

-continued
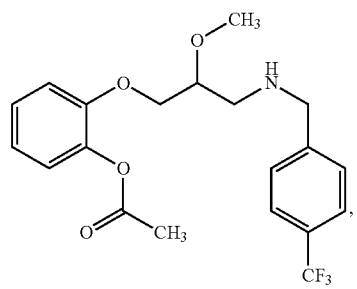
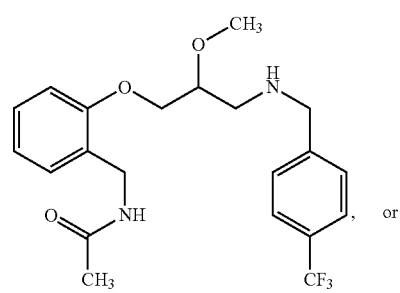
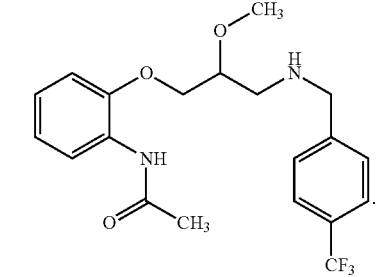
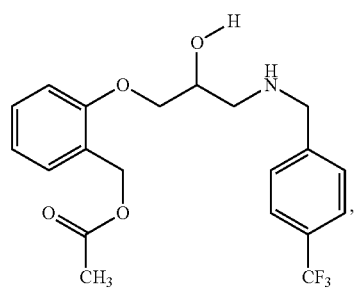
22. The compound of claim 18 having the structure:
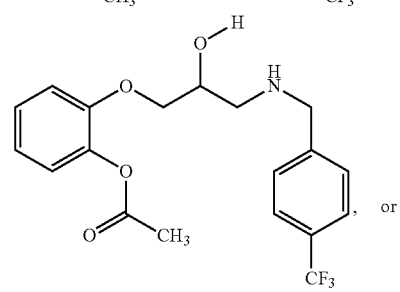
20. The compound of claim 18 having the structure:
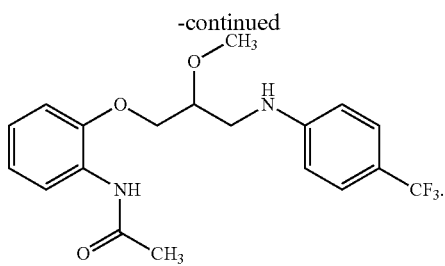
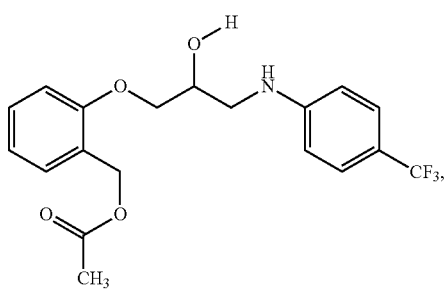
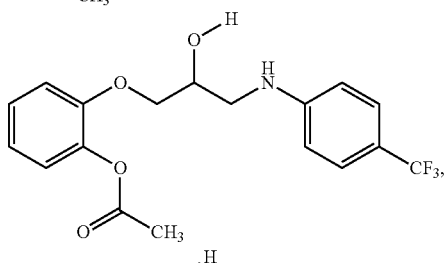
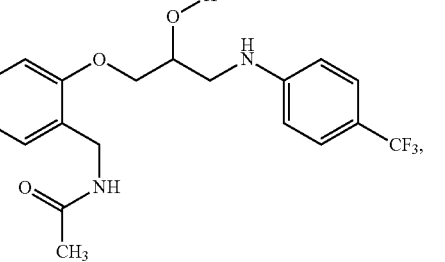
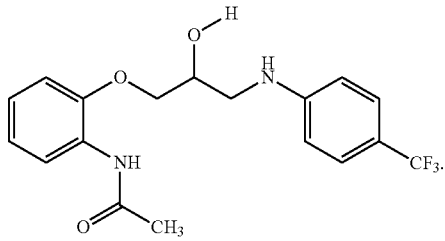
21. The compound of claim 18 having the structure:
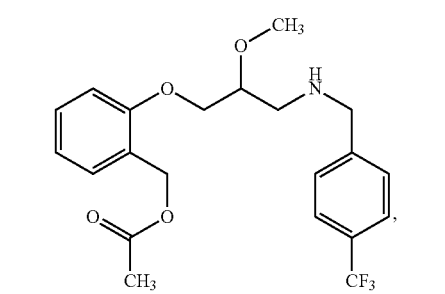

-continued

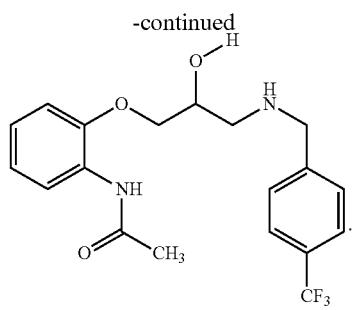

23. A compound of claim 1 that inhibits at least 40% of TNFα induced cytolysis at a concentration of 50 micromolar.

24. A compound of claim 1 that inhibits at least 60% of TNFα induced cytolysis at a concentration of 90 micromolar.

25. A compound of claim 1 that inhibits at least 40% of luciferase activity within 4 hours of incubation with 20 ng/ml TNFα for 4 hours, at a concentration of 75 micromolar of the compound.

26. A compound of claim 1 that inhibits at least 60% of luciferase activity within 4 hours of incubation with 20 ng/ml TNFα for 4 hours, at a concentration of 100 micromolar of the compound.

27. A pharmaceutical composition comprising a compound according to claim 1 or a compound having the structure of formula II

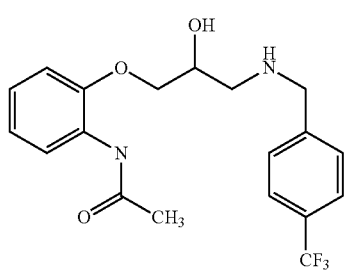

(II)

and a pharmaceutically acceptable excipient.

28. A pharmaceutical composition of claim 27, wherein said compound is present in an amount effective to inhibit the activity of a tumor necrosis factor alpha (TNF-α) protein.

29. A method of treating a patient having an inflammatory disease condition mediated by tumor necrosis factor alpha (TNFα) activity, the method comprising administering to a patient in need of such treatment a therapeutically effective amount of a compound according to claim 1 or a compound having the structure of formula II

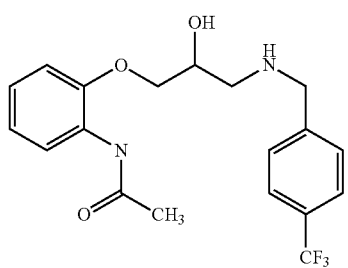

(II)

or a pharmaceutically acceptable salt thereof.

30. The method of claim 29 wherein the compound causes an allosteric change in the conformation of TNF-R.

31. The method of claim 29, wherein the inflammatory disease condition is arthritis.

32. The method of claim 29, wherein the inflammatory disease condition is Crohn's Disease.

33. The method of claim 29, wherein the inflammatory disease condition is inflammatory neuropathy, Lou Gehrig's disease, or Alzheimer's disease.

34. The pharmaceutical composition of claim 27, comprising a compound having the structure of formula II

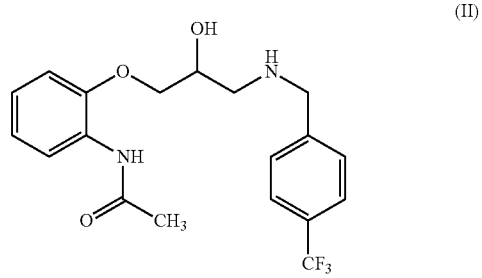 [SMILES: CC(=O)Nc1ccccc1OCC(O)CNCc1ccc(C(F)(F)F)cc1]

(II)

and a pharmaceutically acceptable excipient.

35. The pharmaceutical composition of claim 27, wherein the compound of claim 1 is:

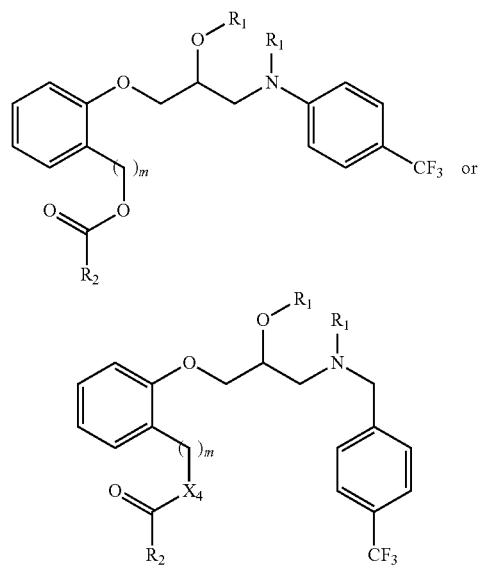

wherein $R_1$ is each independently H, linear or branched $C_{1-3}$ alkyl, or linear or branched $C_{1-3}$ carboxyalkyl and $R_2$ is linear or branched $C_{1-3}$ alkyl.

36. The pharmaceutical composition of claim 27, wherein the compound of claim 1 is:

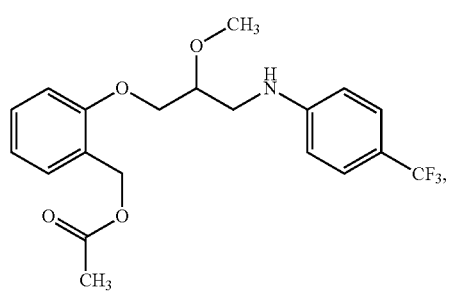

61
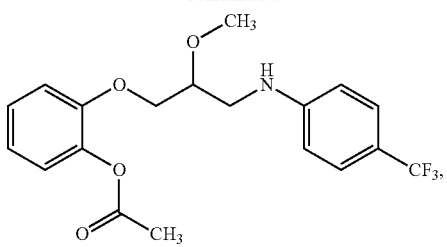
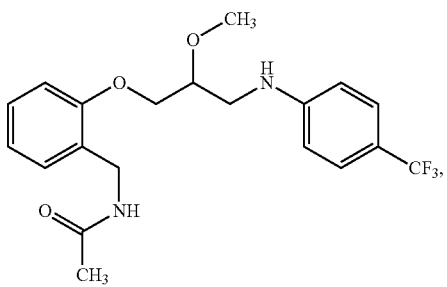
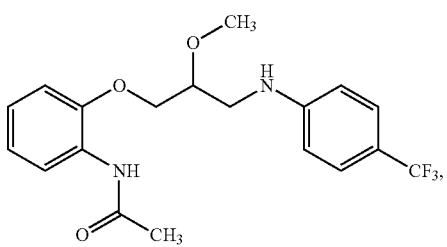
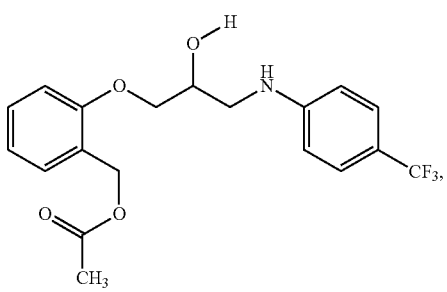
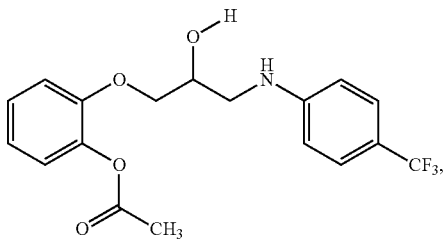
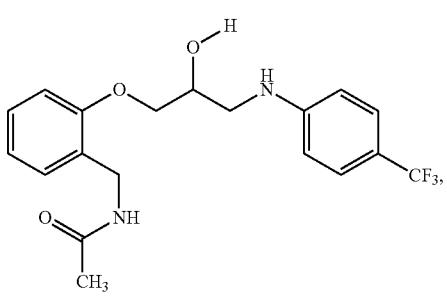
62
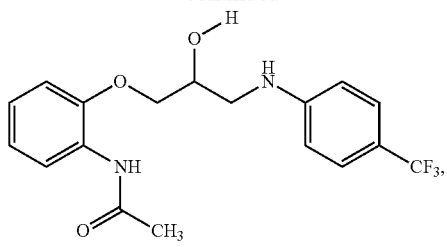
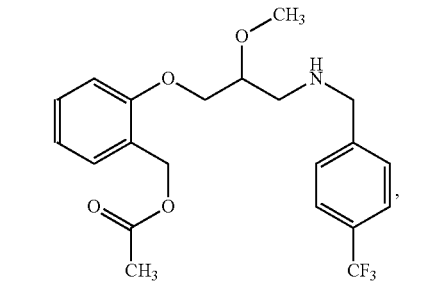
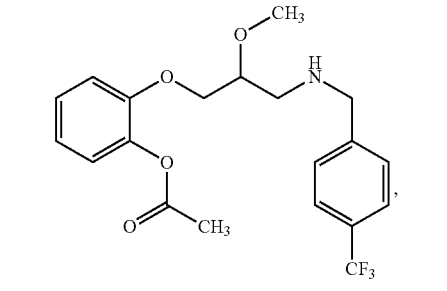
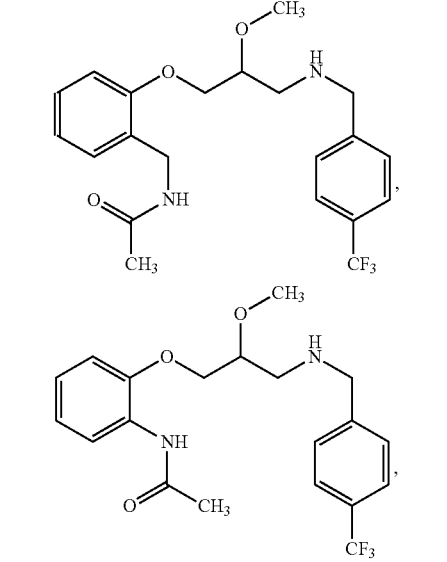
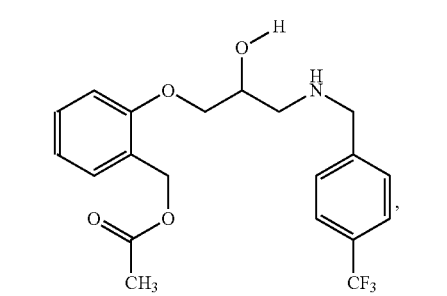

-continued
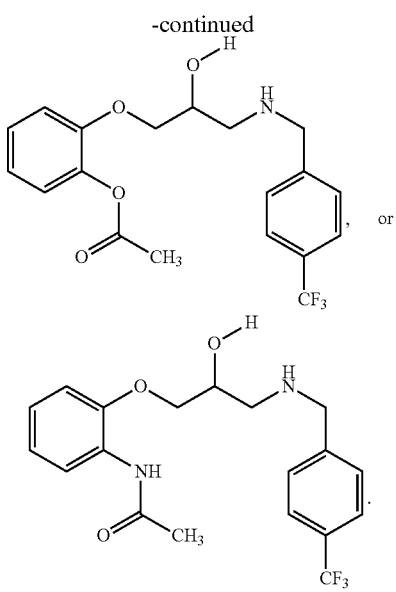
, or
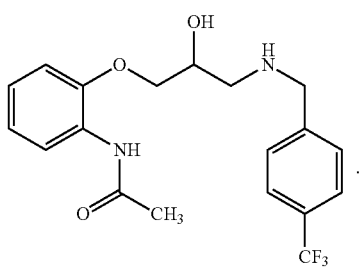
37. The method of claim 29, wherein the compound has the structure of formula II
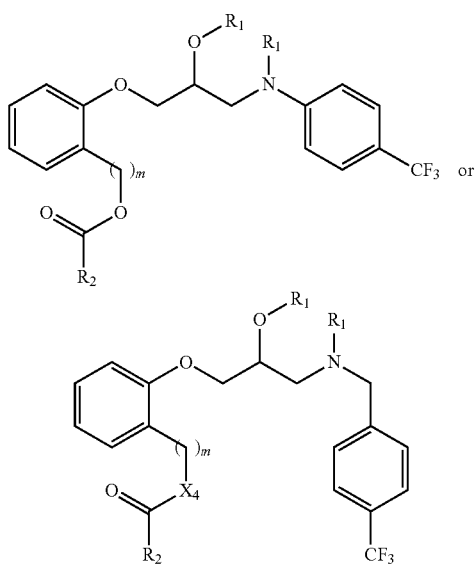
(II)
38. The method of claim 29, wherein the compound of claim 1 is
wherein $R_1$ is each independently H, linear or branched $C_{1-3}$ alkyl, or linear or branched $C_{1-3}$ carboxyalkyl and $R_2$ is linear or branched $C_{1-3}$ alkyl.
39. The method of claim 29, wherein the compound of claim 1 is
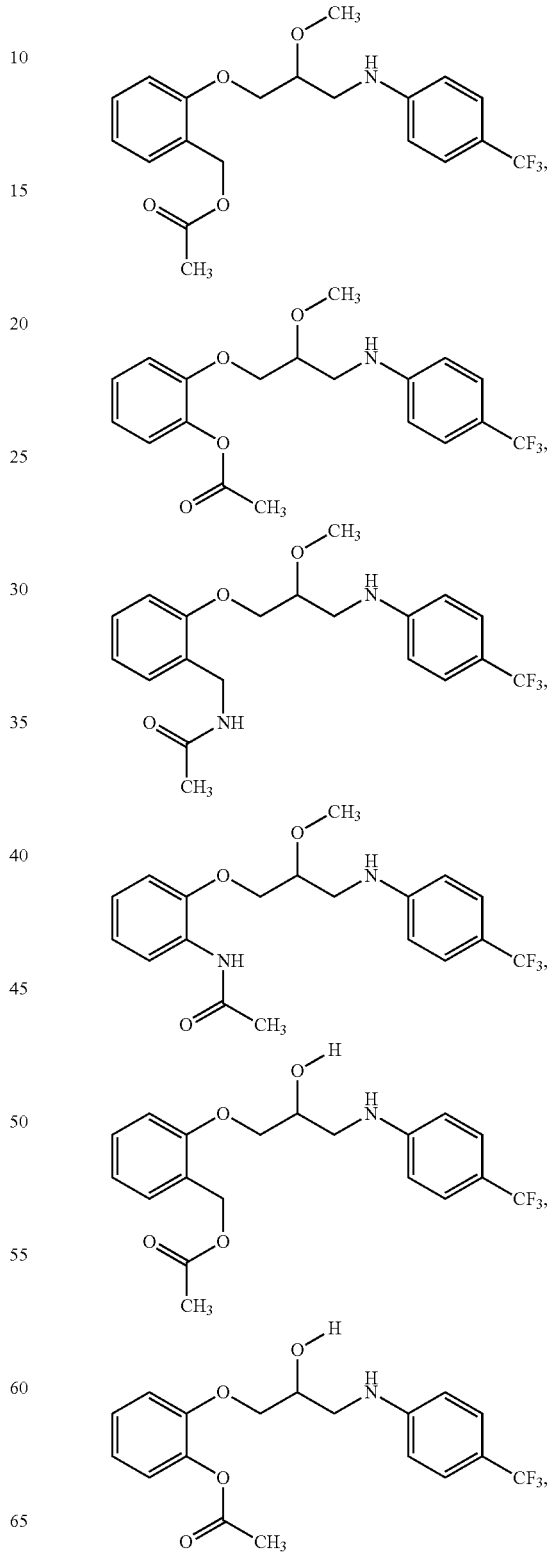

-continued
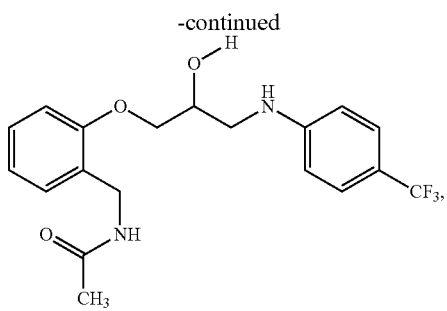
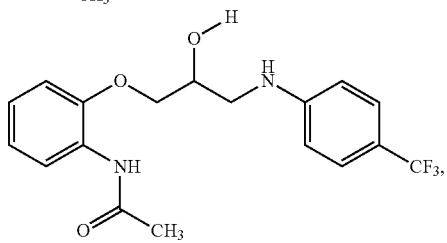
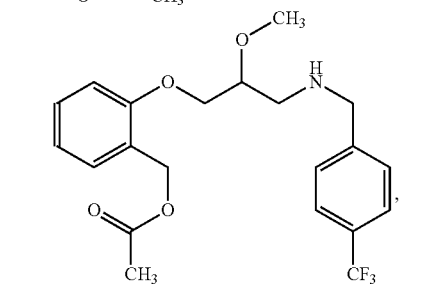
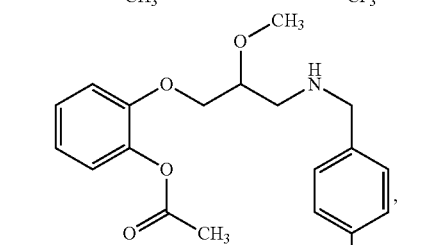
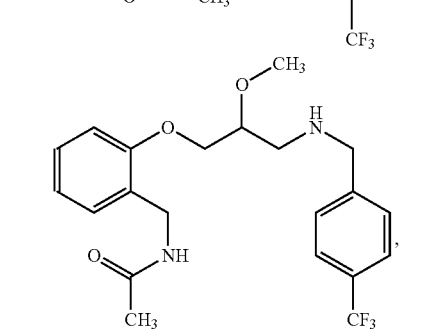
-continued
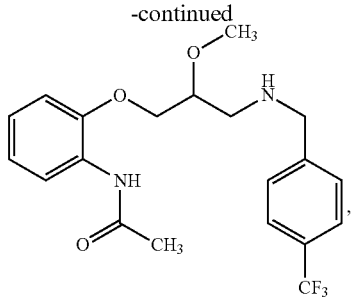
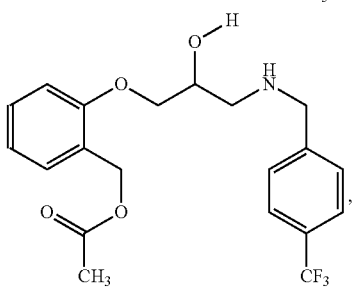
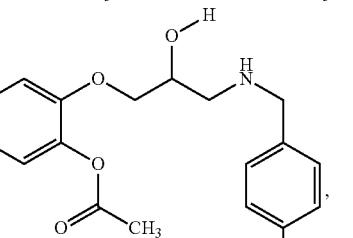
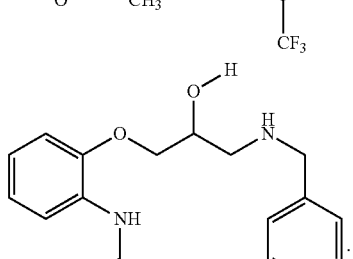, or
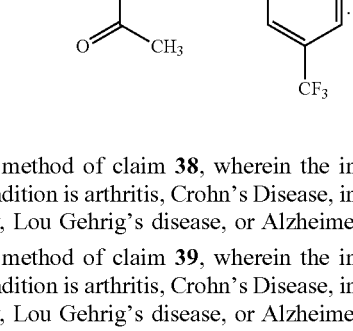.
40. The method of claim 38, wherein the inflammatory disease condition is arthritis, Crohn's Disease, inflammatory neuropathy, Lou Gehrig's disease, or Alzheimer's disease.
41. The method of claim 39, wherein the inflammatory disease condition is arthritis, Crohn's Disease, inflammatory neuropathy, Lou Gehrig's disease, or Alzheimer's disease.
* * * * *